US010180420B2

(12) United States Patent
Bauer-Espindola et al.

(10) Patent No.: US 10,180,420 B2
(45) Date of Patent: Jan. 15, 2019

(54) METHODS FOR DETECTING AN ANALYTE AND PERFORMING A FAILSAFE STEP IN A BODY FLUID USING OPTICAL AND IMPEDANCE MEASUREMENTS

(71) Applicant: Roche Diagnostics Operations, Inc., Indianapolis, IN (US)

(72) Inventors: Klaus Andreas Bauer-Espindola, Mannheim (DE); Carina Horn, Biblis (DE); Michael Marquant, Mannheim (DE); Christine Nortmeyer, Mannheim (DE); Volker Unkrig, Ladenburg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 14/963,576

(22) Filed: Dec. 9, 2015

(65) Prior Publication Data
US 2016/0091482 A1 Mar. 31, 2016

Related U.S. Application Data

(63) Continuation of application No. PCT/EP2014/053517, filed on Feb. 24, 2014.

(30) Foreign Application Priority Data

Jun. 10, 2013 (EP) ..................................... 13171208

(51) Int. Cl.
G01N 27/02 (2006.01)
G01N 33/49 (2006.01)
G01N 27/327 (2006.01)
G01N 21/64 (2006.01)
G01N 21/78 (2006.01)
G01N 21/84 (2006.01)
G01N 27/12 (2006.01)
G01N 21/77 (2006.01)

(52) U.S. Cl.
CPC ....... G01N 33/492 (2013.01); G01N 21/6428 (2013.01); G01N 21/78 (2013.01); G01N 21/8483 (2013.01); G01N 27/02 (2013.01); G01N 27/12 (2013.01); G01N 27/3274 (2013.01); G01N 2021/7786 (2013.01)

(58) Field of Classification Search
None
See application file for complete search history.

(56) References Cited

U.S. PATENT DOCUMENTS

| 5,601,995 | A | 2/1997 | Exner | |
|---|---|---|---|---|
| 6,797,150 | B2 | 9/2004 | Kermani et al. | |
| 7,276,147 | B2 * | 10/2007 | Wilsey | C12Q 1/001 204/403.04 |
| 7,338,639 | B2 | 3/2008 | Burke et al. | |
| 7,407,811 | B2 | 8/2008 | Burke et al. | |
| 7,452,457 | B2 * | 11/2008 | Burke | G01N 27/3274 205/775 |
| 7,494,816 | B2 | 2/2009 | Burke et al. | |
| 7,547,382 | B2 * | 6/2009 | Harding | G01N 27/327 204/403.01 |
| 7,641,785 | B2 | 1/2010 | Shinno et al. | |
| 7,981,363 | B2 | 7/2011 | Burke et al. | |
| 8,088,271 | B2 | 1/2012 | Fujiwara et al. | |
| 9,255,286 | B2 * | 2/2016 | Horn | G01N 21/78 |
| 9,307,935 | B2 * | 4/2016 | Pluta | A61B 5/0531 |
| 9,670,524 | B2 * | 6/2017 | Horn | C12Q 1/54 |
| 2002/0146835 | A1 | 10/2002 | Modzelewski et al. | |
| 2004/0036485 | A1 | 2/2004 | Sullivan | |
| 2004/0260511 | A1 | 12/2004 | Burke et al. | |
| 2007/0017824 | A1 * | 1/2007 | Rippeth | G01N 27/3272 205/792 |
| 2007/0102292 | A1 | 5/2007 | Dreibholzet et al. | |
| 2007/0264421 | A1 | 11/2007 | Meier et al. | |
| 2008/0083618 | A1 | 4/2008 | Neel et al. | |
| 2008/0202928 | A1 | 8/2008 | Hyun et al. | |
| 2009/0089010 | A1 | 4/2009 | Burke et al. | |
| 2009/0170210 | A1 | 7/2009 | Fukunaga et al. | |
| 2011/0139634 | A1 | 6/2011 | Chou et al. | |
| 2011/0155590 | A1 | 6/2011 | Huffstodt et al. | |
| 2011/0168575 | A1 * | 7/2011 | Lica | G01N 27/3274 205/782 |

(Continued)

FOREIGN PATENT DOCUMENTS

| EP | 0816849 B1 | 1/1998 |
|---|---|---|
| EP | 0821234 A2 | 1/1998 |

(Continued)

OTHER PUBLICATIONS

International Search Report dated May 22, 2014 in Application No. PCT/EP20141053517, 4 pages.

(Continued)

Primary Examiner — Ralph J Gitomer
(74) Attorney, Agent, or Firm — Woodard, Emhardt, Moriarty, McNett and Henry, LLP

(57) ABSTRACT

A method for detecting at least one analyte in a body fluid is disclosed comprising performing an optical measurement, wherein at least one test chemical is contacts the body fluid. The test chemical is an optical test chemical adapted to perform at least one detection reaction, wherein at least one optically detectable property is changed due to the detection reaction to provide at least one optical measurement value. At least one impedance measurement is generated wherein at least one alternating electrical signal is applied to the body fluid via the impedance measurement electrodes and at least one answer signal is recorded, and at least one impedance measurement value is generated. At least one evaluation step is performed wherein at least one evaluation algorithm is used, and the optical measurement value and the impedance measurement value are used for determining a concentration of the analyte in the body fluid.

15 Claims, 9 Drawing Sheets

(56) References Cited

U.S. PATENT DOCUMENTS

| | | |
|---|---|---|
| 2012/0031777 A1 | 2/2012 | Burke et al. |
| 2012/0247956 A1 | 10/2012 | Chou et al. |
| 2012/0329144 A1* | 12/2012 | Kwak ............... B01L 3/502746 435/287.3 |
| 2013/0199944 A1* | 8/2013 | Petisee ................. A61B 5/1486 205/778 |
| 2013/0217054 A1 | 8/2013 | Huffstodt et al. |
| 2015/0286778 A1* | 10/2015 | Aigner ................. G01N 21/274 436/70 |
| 2016/0018246 A1* | 1/2016 | Bohm ............... G01N 27/3274 73/1.02 |

FOREIGN PATENT DOCUMENTS

| | | |
|---|---|---|
| EP | 1037048 A2 | 9/2000 |
| EP | 1394545 A1 | 3/2004 |
| EP | 2306190 A1 | 4/2011 |
| JP | 2007303968 A | 11/2007 |
| WO | WO 1994/016095 | 7/1994 |
| WO | WO 2004/017050 | 2/2004 |
| WO | 2004/113910 A1 | 12/2004 |
| WO | WO 2005/098424 A1 | 10/2005 |
| WO | 2005/114163 A1 | 12/2005 |
| WO | WO 2007/063963 A1 | 5/2007 |
| WO | 2007/064576 A1 | 6/2007 |
| WO | 2008/040998 A2 | 4/2008 |
| WO | 2011/081437 A2 | 7/2011 |
| WO | WO 2011/104517 A2 | 9/2011 |
| WO | WO 2013/036493 A1 | 3/2013 |

OTHER PUBLICATIONS

Hoenes, Joachim et al., The Technology Behind Glucose Meters: Test Strips, Diabetes Technology & Therapeutics, 2008, pp. S-10-S-26, vol. 10, Supplement 1.

Young, I. T. et al., Monitoring enzymatic reactions in nanolitre wells, Journal of Microscopy, 2003, pp. 254-263, vol. 212, Part 3.

* cited by examiner

METHODS FOR DETECTING AN ANALYTE AND PERFORMING A FAILSAFE STEP IN A BODY FLUID USING OPTICAL AND IMPEDANCE MEASUREMENTS

CROSS-REFERENCE TO RELATED APPLICATIONS

This application is a continuation of International Patent Application No. PCT/EP2014/053517 filed Feb. 24, 2014, which claims priority to European Patent Application No. 13171208.5 filed Jun. 10, 2013, the disclosures of which are hereby incorporated by reference in their entirety.

FIELD OF THE INVENTION

The present invention discloses a method, a test element and a measurement system for detecting at least one analyte in a body fluid. Further, a use of aluminum as an electrode material for electrodes for performing impedance measurements in a body fluid is disclosed. The methods, systems and use according to the present invention may be used for determining the concentration of glucose in one or more body fluids, such as in whole blood. Additionally or alternatively, however, one or more other types of analytes and/or one or more other types of body fluids may be used. The invention preferably may be applied in the field of diabetes care, both in home monitoring and in hospital applications. Additionally or alternatively, other uses are feasible.

In the art, a large number of devices and methods for determining the presence and/or the concentration of one or more analytes in body fluids are known. Without restricting the scope of the present invention, in the following, mainly reference is made to the determination of glucose as an exemplary and preferred analyte.

For performing fast and simple measurements, several types of test elements are known, which are based on the use of a test chemical, i.e. on the use of one or more chemical compounds or chemical mixtures adapted for performing a detection reaction for detecting the analyte. The test chemical often is also referred to as a test substance, a test chemistry, a test reagent or as a detector substance. For details of potential test chemicals and test elements comprising such test chemicals, which may also be used within the present invention, reference may be made to J. Hoenes et al.: The Technology Behind Glucose Meters: Test Strips, Diabetes Technology & Therapeutics, Vol. 10, Supplement 1, 2008, S-10 to S-26. Other types of test elements and/or test substances are feasible and may be used within the present invention.

By using one or more test chemicals, a detection reaction may be initiated, the course of which depends on the concentration of the analyte to be determined. Typically, as may also be the case in the present invention, the test chemical is adapted to perform at least one detection reaction when the analyte is present in the body fluid, wherein the extent and/or the degree of the detection reaction typically depends on the concentration of the analyte. Generally, the test chemical may be adapted to perform a detection reaction in the presence of the analyte, wherein at least one detectable property of at least one of the body fluid and the test chemical is changed due to the detection reaction. The at least one detectable property generally may be selected from a physical property and a chemical property. In the following, without restricting potential other embodiments, reference will be made to detection reactions in which one or more physical properties are changed due to the detection reaction, such as one or more of at least one electrical property and at least one optical property. Further, without restricting alternative solutions, reference will be made to detection reactions in which at least one optically detectable property of at least one of the body fluid and the test chemical is changed due to the detection reaction. This at least one optically detectable property generally may be detected by detecting light propagating from the test chemical to a detector. This light, which may also be referred to as the detection light, generally may be light emitted by the test chemical itself and/or may be light which is elastically and/or inelastically scattered or reflected by the test chemical. Thus, the light may be luminescence light, preferably fluorescence light, the generation of which may be excited by excitation light illuminating the test chemical. Additionally or alternatively, the light may be light which is reflected by the test chemical, such as by reflecting and/or scattering primary light. In the latter case, the test chemical preferably may be adapted to change at least one reflective property due to the detection reaction, preferably a color.

For deriving the concentration of the analyte, the progress of the detection reaction may be monitored by measuring and/or monitoring a time development of at least one measurement value indicating the progress of the detection reaction. This measurement value generally may comprise an arbitrary measurement value which is linked to the detection reaction, such as an optical measurement value. As an example, in many measurement setups, optical measurement values are monitored, such as a remission of a test field containing the test substance. By recording the time development of at least one measurement value, a measurement curve is provided.

A major challenge resides in a fast and, still, reliable and precise determination of the analyte concentration from the at least one measurement value, such as from a measurement curve comprising a plurality of measurement values. For this purpose, a large number of methods and devices are known in the art.

Most of the methods and devices known in the art are not suited to take into account the fact that the detection reaction itself may be influenced by one or more disturbances other than the concentration of the analyte itself. Specifically, the determination of the concentration of the analyte may be disturbed by the presence of one or more substances other than the analyte to be determined, the substances influencing at least one of the detection reaction itself and/or the determination of the at least one measurement value. These substances are generally referred to as "interferents". Thus, specifically, in many types of test chemicals and test elements, the concentration of particulate components in the body fluid may have a significant impact on the measurement results. As an example, the concentration of cellular components within the body fluid to be analyzed, such as the so-called hematocrit (in the following HKT, also referred to as HCT), is known to have an influence on the analyte concentration as determined by standard test elements, such as glucose test strips. This influence may be due to the fact that the rheological properties and/or sample propagation properties as well as diffusion processes are significantly altered by the presence of particulate components such as blood cells. Besides the hematocrit, other interferents are known, such as ascorbic acid or glutathione. Additionally or alternatively, redox active drugs may be named. Further, one or more interferents may be present which are capable of performing at least one redox reaction with the at least one test chemical and/or with the body fluid and/or the analytes to be detected. As an example, a plurality of pharmaceuticals, peroxides or substances present in typical disinfectants are adapted to perform redox reactions. As mentioned above, methods and devices known in the art typically are not suited to take into account these disturbances when evaluating measurement curves for the purpose of determining the analyte concentration.

It has been known that measurement of a soluble analyte in a suspension additionally comprising at least one particulate compound is hampered by the fact that the measured value may deviate from the actual concentration depending on the concentration of said particulate compound. For the example of determining blood glucose levels, it has been proposed to use viscosity of the sample as a surrogate measure of the concentration of blood cells, i.e. the hematocrit (JP 2007/303 968). However, the viscosity of a blood sample depends on several other parameters, such as the concentration of fibrinogen and globulins, red blood cell and platelet aggregation, and the like, so the correction derived from direct or indirect viscosity measurement is less than ideal.

In US 2011/0155590 A1, a method for determining concentrations of a plurality of analytes from a single blood sample placed in a single opening is disclosed. A portion of the single blood sample is absorbed by a test matrix that includes a plurality of layers and a chromogenic agent. A colored response is generated by the test matrix. The colored response is proportional to the concentration of a first analyte. A portion of the single blood sample is drawn into a capillary tube and placed in contact with an electrode and a counter electrode. An electrical property of the single blood sample is analyzed through the electrode and counter electrode. The electrode property is proportional to the concentration of a second analyte in the single blood sample.

In US 2008/0202928 A1, a multi-layer strip for use in measuring biological material and a system for measuring a biological material are disclosed. The multi-layer strip includes a stack of a plurality of strips, each having a flow channel and a reaction unit. Further, a system for measuring a biological material is disclosed, comprising the multi-layer strip, and further, comprising a combination of an optical processing module and an electrochemical processing module.

In U.S. Pat. No. 7,407,811 B2, U.S. Pat. No. 7,494,816 B2, U.S. Pat. No. 7,338,639 B2 and U.S. Pat. No. 7,981,363 B2, methods of measuring an analyte in a biological fluid are disclosed. Therein, an excitation signal having a DC component and an AC component is applied. The responses are measured, and a corrected DC response is determined using the AC response. Further, a concentration of the analyte is determined based upon the corrected DC response.

DE 20 2010 016 517 U1 discloses a biosensor test strip for measuring an analyte concentration. The test strip has a base and an electrode layer on the base which comprises a first set of electrodes and a second set of electrodes. The first set of electrodes is used for measuring the analyte concentration, and the second set of electrodes is used for measuring a hematocrit.

EP 0 816 849 B1 discloses a method for measuring the concentration of an analyte in whole blood which comprises the use of light of more than one wavelength, wherein a first wavelength, which can be absorbed by a light-absorptive dye product, and a second wavelength, which can be absorbed by whole blood, are used. By measuring reflected light of the second wavelength, a background reading is generated for correcting a measurement of the analyte. Similarly, EP 1 037 048 A2 discloses a quantitative analysis of glucose or cholesterol in a whole blood sample employing a united multi-layer analytical element which contains several reagents. Optionally, a hematocrit value may be determined by using a calibration curve which indicates a relationship between a deviation of a hematocrit value from the predetermined hematocrit value and a deviation of a concentration of glucose or cholesterol.

In U.S. Pat. No. 8,088,271 B2, a method of electrochemically measuring hematocrit value is disclosed. Therein, for electrochemically measuring the hematocrit value, an electrode system having a working electrode and a counter electrode is used, wherein, on the counter electrode, a redox substance is provided. Blood is supplied to the electrode system, and a voltage is supplied to the electrode system in this state, in order to cause an oxidation current or a reduction current to flow between the working electrode and the counter electrode. The hematocrit value is determined based on a value of the detected current.

In U.S. Pat. No. 7,641,785 B2, a sensor for blood component analysis is disclosed. The sensor can correct the effect of a hematocrit. The sensor includes an analysis portion including a working electrode, a counter electrode and a reagent portion. The reagent portion includes an oxidoreductase that reacts with the blood component, and a mediator. The blood component is measured by causing a redox reaction between the blood component and the oxidoreductase in the presence of the mediator and detecting a redox current. Further, a hemolyzing agent is disclosed, wherein the erythrocytes are hemolyzed with the hemolyzing agent so as to cause hemoglobin released to an outside of the erythrocyte to react with the mediator. A current is generated by this reaction and is detected, in order to correct an effect of a hematocrit.

EP 2 306 190 A1 discloses a method for measuring target components in erythrocyte-containing specimen. Firstly, prior to measurement, a relationship between amounts of the target component and a plurality of signals corresponding thereto is provided. Then, a plurality of signals derived from the target component in the erythrocyte-containing specimen are acquired with a biosensor. With reference to the relationship, the amount of the target component in the specimen is determined based on the thus-acquired plurality of signals.

In WO 2005/114163 A1, methods and devices for performing in-situ hematocrit adjustments during glucose testing are disclosed. In these methods and devices, a resistance of blood sample is measured using a biosensor reagent. Further, a resistance of plasma is measured, and the resistance of red blood cells is calculated. Therefrom, a hematocrit is calculated, and a glucose value is adjusted.

WO 2008/040998 A2 discloses methods and systems for determining a substantially hematocrit-independent analyte concentration. A test strip including a reference electrode and a working electrode is used, wherein the working electrode is coated with a reagent layer. By using a test meter, a plurality of voltages is applied to the reference electrode and the working electrode over respective durations. A signal processor is used in order to determine a substantially hematocrit-independent concentration of the analyte from a plurality of current values as measured by the processor upon application of a plurality of test voltages.

US 2007/0102292 A1 discloses a method and a corresponding system for error checking an electrochemical sensor having at least two electrodes and a liquid measuring medium applied thereto. The method comprises determining a first admittance between a first set of electrodes of the sensor; determining a second admittance between a second set of electrodes of the sensor; determining a value using the first admittance and the second admittance; and displaying an error message if the value is out of a predetermined tolerance.

Further, in the art, a variety of electrode structures is generally known. Thus, as an example, WO 2004/113910 A1 discloses a system for testing for analytes in a sample of biological fluid includes a test strip that defines a cavity for receiving the sample. At least two sets of electrodes are adjacent the sample cavity, including one for measuring one property of the sample, and another for measuring one or more other properties of the sample, such as temperature and/or the presence or magnitude of confounding variables. The measurements are combined to yield the desired result. At least one set of working and counter electrodes each have a plurality of elongated "fingers" interdigitated with those of the other electrode in the set. The gaps between fingers can be quite small, so that the two electrode sets together can operate in a small measurement volume of sample. Additional electrodes can be included that measure the presence or sufficiency of the sample.

Further, a plurality of electrode materials for determining analyte concentrations is known in the art. Thus, as an example, DE 20 2012 101 156 U1 discloses a biosensor test strip having a base and an electrode layer on a first surface of the base. The electrode layer comprises a first electrode pattern which is formed by using a first electrically conductive material. Further, a second electrode pattern is provided, which comprises a second electrically conductive material. The second electrically conductive material consists of a noble metal, whereas the first electrically conductive material does not consist of a noble metal. Various metals are disclosed. US 2007/0264421 A1 discloses a method for producing multiple layer systems on a nonconductive substrate. Metallic layers and electrically non-conductive layers are alternately deposited respectively by means of PVD and PECVD and are modified in such a way that at least one layer can be optionally selectively structured. Selective structuring by means of laser energy is possible by introducing sacrificial layers. Specifically, a method for manufacturing a test sensor is disclosed which implies the use of laser patterning. Again, various electrode materials are disclosed.

In US 2008/0083618 A1, methods and devices for determining the concentration of a constituent in a physiological sample are disclosed. A blood sample is introduced into a test strip with portions of the blood sample being directed to both a first capillary and a second capillary. The first capillary is configured to electrochemically determine a concentration of a first analyte in a blood sample by measuring a signal across a set of electrodes. The second capillary is configured to determine a hematocrit value of the blood sample by measuring a signal across a second set of electrodes.

WO 2011/081437 A2 discloses a sample analysis cartridge and a sample cartridge reader. In measuring a particular component included in a sample flowing in a microfluidic channel, a numerical value of hematocrit is reflected to thus improve the accuracy of measurement of the particular component.

In T. Young et al.: "Monitoring enzymatic reactions in nanoliter wells", Journal of Microscopy, vol. 212, No. 3, 3 Dec. 2003, pp. 254-263, a lab-on-a-chip micro array system is disclosed, based on nanoliter capacity wells. Further, methods for determining a fluid volume per well are disclosed, the methods being based on impedance measurements within the wells.

In US 2004/0036485 A1, osmolarity measurements of a sample fluid, such as tear film, are disclosed, the measurements being achieved by depositing an aliquot-sized sample on a sample receiving substrate. The sample fluid is placed on a sample region of the substrate. Energy is imparted to the sample fluid and energy properties of the fluid can be detected to produce a sample fluid reading that indicates osmolarity of the sample fluid. The imparted energy can comprise electrical, optical or thermal energy. In the case of electrical energy, the energy property of the sample fluid can comprise electrical conductivity. The substrate can be packaged into a chip, such as by using semiconductor fabrication techniques.

Despite the technical progress involved by the above-mentioned devices and methods disclosed in the art, a large number of disadvantages and technical challenges still remain. Thus, firstly, still a need for simple and, still, reliable means and methods exists, which are suited for correcting a measured analyte concentration, such as a glucose concentration, for one or more interferents. Specifically, both in home monitoring and in hospital applications, interferents such as pharmaceuticals and/or disinfectants, as well as redox-active substances such as ascorbic acid, glutathione and peroxides, which may generate additional signals, shall be corrected for. As opposed to known methods and systems, besides an increased reliability of the correction, a simplified setup of the algorithm and/or a simplified setup of the correction measurement itself is highly desirable. Thus, as an example, a separation of cellular components from whole blood in many cases causes a high effort and involves a high consumption of measurement time.

Further, in known methods and devices, disadvantages arise from the electrode materials which are used. Thus, typically, gold or other inert conductive materials are used. These materials, however, which exhibit significant electroactive properties, allow for significant Faradayic con-versions, dependent on the electrode potentials. Consequently, an arbitrary redox-active component such as pharmaceuticals, which are converted at these electrodes, may falsify measurements by using these electrodes. Specifically, this may be the case for transition metal elements. In addition, adverse electrode effects such as electrode fouling and/or absorption effects may occur. Further, additionally, many electrical measurements known in the art are made by using coated electrodes. Coated electrodes, however, imply a plurality of phase transitions including various multi-layer capacities. The high capacitances induced by these multilayer setups falsify a large number of electrical measurements, such as measurements using alternating voltages and/or currents.

It is therefore an objective of the present invention to provide methods and devices for determining the concentration of an analyte in a body fluid which overcome the above-mentioned shortcomings and challenges of known methods and devices. Specifically, methods and devices shall be disclosed which may easily be implemented into laboratory, hospital and patient self-testing (PST) applications and which are capable of reliably correcting an analyte concentration for the presence of one or more interferents or disturbances.

SUMMARY OF THE INVENTION

This problem is solved by a method, a test element and a measurement system for detecting at least one analyte in a body fluid as well as by specific uses, with the features of the independent claims. Additional embodiments, which might be realized in an isolated fashion or in any arbitrary combination, are listed in the dependent claims.

As used in the following, the terms "have", "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B", "A comprises B" and "A includes B" may both refer to a situation in which, besides B, no other element is present in A (i.e. a situation in which A solely and exclusively consists of B) and to a situation in which, besides B, one or more further elements are present in entity A, such as element C, elements C and D or even further elements.

Various embodiments are summarized as follows:

A. A method for detecting at least one analyte in a body fluid, the method comprising the following steps:
 a) performing an optical measurement, wherein at least one test chemical is contacted with the body fluid, wherein the test chemical is an optical test chemical and is adapted to perform at least one detection reaction in the presence of the analyte, wherein at least one optically detectable property of at least one of the body fluid and the test chemical is changed due to the detection reaction, wherein at least one optical measurement value is generated;
 b) performing at least one impedance measurement, wherein at least two impedance measurement electrodes are used, wherein at least one alternating electrical signal is applied to the body fluid via the impedance measurement electrodes and wherein at least one answer signal is recorded, wherein at least one impedance measurement value is generated;
 c) performing at least one evaluation step, wherein, in the evaluation step, at least one evaluation algorithm is used, wherein the optical measurement value and the impedance measurement value are used for determining a concentration of the analyte in the body fluid, wherein step c) comprises at least one failsafe step, wherein, in the failsafe step, only the impedance measurement value is used.

B. The method according to embodiment A, wherein the failsafe step comprises comparing at least one parameter with at least one threshold value.

C. The method according to embodiment B, wherein the at least one parameter is selected from the group consisting of: an interferent concentration; an environmental parameter; an experimental parameter; a sample parameter.

D. The method according to embodiment B, wherein the at least one parameter is selected from the group consisting of: an interferent concentration; an environmental parameter; a sample parameter.

E. The method according to embodiment A, wherein in step c), the concentration of the analyte in the body fluid is a corrected concentration which is corrected for at least one interferent concentration in the body fluid.

F. The method according to embodiment A, wherein step c) comprises the following substeps:
 c.1) determining an estimated value of the concentration of the analyte in the body fluid by using the optical measurement value and a first evaluation algorithm;
 c.2) determining a corrected value of the concentration of the analyte in the body fluid by using the estimated value and correcting the estimated value by using at least one correction algorithm, wherein the correction algorithm uses the impedance measurement value.

G. The method according to embodiment A, wherein a single test element is used for both method step a) and method step b).

H. The method according to embodiment A, wherein at least one impedance measurement electrode of the at least two impedance measurement electrodes comprises a metal selected from the group consisting of: aluminum, molybdenum, tungsten, tantalum, niobium, zirconium, titanium, ruthenium, rhodium, iridium, palladium, platinum, silver, gold.

I. The method according to embodiment A, wherein at least one impedance measurement electrode of the at least two impedance measurement electrodes comprises aluminum.

J. The method according to embodiment A, wherein a wetting control of at least one element selected from the group consisting of the impedance measurement electrodes, the test chemical and a capillary element is performed by using the impedance measurement value.

K. A test element for detecting at least one analyte in a body fluid, wherein the test element is adapted for use in the method according to embodiment A, the test element comprising:
 a) at least one test chemical which may be contacted with the body fluid, the test chemical being an optical test chemical and being adapted to perform at least one detection reaction in the presence of the analyte, wherein at least one optically detectable parameter of at least one of the body fluid and the test chemical is changed due to the detection reaction;
 b) at least two impedance measurement electrodes adapted for applying an alternating electrical signal to the body fluid and adapted to record at least one answer signal;
 wherein the test element comprises at least one application location, wherein a sample of the body fluid is applicable to the application location, wherein the test element further comprises at least one capillary element, wherein the capillary element is adapted for conducting the sample of the body fluid from the application location to at least one of the test chemical and the impedance measurement electrodes.

L. The test element according to embodiment K, wherein at least one impedance measurement electrode of the at least two impedance measurement electrodes comprises a metal selected from the group consisting of: aluminum, molybdenum, tungsten, tantalum, niobium, zirconium, titanium, ruthenium, rhodium, iridium, palladium, platinum, silver, gold.

M. The test element according to embodiment K, wherein at least one impedance measurement electrode of the at least two impedance measurement electrodes comprises aluminum.

N. The test element according to embodiment K, wherein the impedance measurement electrodes are bare metal electrodes and wherein the impedance measurement electrodes are in direct contact with the body fluid during the impedance measurement.

O. The test element according to embodiment K, wherein the test element comprises at least one substrate and the at least two impedance measurement electrodes applied to the substrate, wherein the test element further comprises at least one test field connected to the substrate, wherein the test field comprises the test chemical.

P. A measurement system for detecting at least one analyte in a body fluid, the measurement system comprising:

i) at least one test element according to embodiment K;
ii) at least one measurement device adapted for using the test element, wherein the measurement device is adapted to perform the method according to embodiment A.

Q. The measurement system according to embodiment P, wherein the measurement device comprises at least one optical detector, wherein the optical detector is adapted to measure the at least one optically detectable property and to generate the at least one optical measurement value, wherein the measurement device further comprises at least one impedance measurement device, wherein the impedance measurement device is connectable to the impedance measurement electrodes and wherein the impedance measurement device is adapted to perform the impedance measurement.

R. The measurement system according to embodiment P, wherein the measurement device further comprises at least one evaluation unit, wherein the evaluation unit is adapted to determine the concentration of the analyte in the body fluid by performing at least one evaluation algorithm, by using the at least one optical measurement value and the at least one impedance measurement value.

S. The method according to embodiment C, wherein the at least one parameter is an interferent concentration, wherein the interferent concentration is a hematocrit.

T. The method according to embodiment C, wherein the at least one parameter is an environmental parameter, wherein the environmental parameter is a temperature of a surrounding environment.

U. The method according to embodiment C, wherein the at least one parameter is an experimental parameter, wherein the experimental parameter is one or both of a degree of filling of a capillary element and a degree of wetting of a test chemical.

V. The method according to embodiment C, wherein the at least one parameter is a sample parameter, wherein the sample parameter is a sample temperature.

W. The method according to embodiment D, wherein the at least one parameter is an interferent concentration, wherein the interferent concentration is a hematocrit.

X. The method according to embodiment D, wherein the at least one parameter is an environmental parameter, wherein the environmental parameter is a temperature of a surrounding environment.

Y. The method according to embodiment D, wherein the at least one parameter is a sample parameter, wherein the sample parameter is a sample temperature.

BRIEF DESCRIPTION OF THE FIGURES

Further optional features and embodiments of the invention will be disclosed in more detail in the subsequent description of preferred embodiments, preferably in conjunction with the dependent claims. Therein, the respective optional features may be realized in an isolated fashion as well as in any arbitrary feasible combination, as the skilled person will realize. The scope of the invention is not restricted by the preferred embodiments. The embodiments are schematically depicted in the Figures. Therein, identical reference numbers in these Figures refer to identical or functionally comparable elements.

In the Figures.

DETAILED DESCRIPTION OF THE INVENTION

Figure 1:
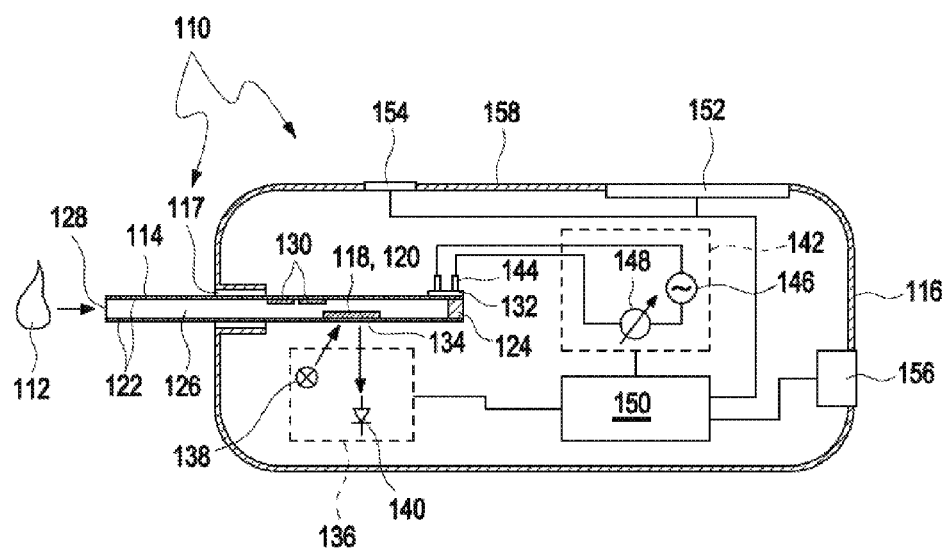
FIG. 1 shows a cross-sectional view of an exemplary embodiment of a measurement system, a test strip and a measurement device according to the present invention.

In a first aspect of the present invention, a method for detecting at least one analyte in a body fluid is disclosed. As used herein, detecting generally refers to a qualitative and/or quantitative determination of the presence of a substance and/or an object. Thus, generally, the detecting may refer to gaining at least one item of information regarding the presence and/or the concentration of the substance. Preferably, the concentration of the analyte in the body fluid is determined.

The body fluid generally may be or may be selected from an arbitrary type of body fluid, preferably from the group consisting of: blood, preferably whole blood; interstitial fluid; urine; saliva. Additionally or alternatively, other types of body fluids may be used. Additionally or alternatively, also further processed body fluids like blood plasma or blood serum may be used.

The analyte generally may be a substance or compound or a combination of substances or compounds which may be present in the body fluid. The analyte may be a substance which is part of a metabolism of a human or animal being or which may take part in the metabolism. Specifically, the analyte may be a metabolite. Preferably, the analyte is selected from the group consisting of: glucose, lactate, triglycerides, ketone, ethanol, total cholesterol, HDL cholesterol, LDL cholesterol, urea, uric acid, creatinine, GOT, GPT, GGT, ammonia. Additionally or alternatively, also other clinical chemical parameters or analytes like alkaline phosphatase (ALP), creatine kinase (CK), amylaea, pancraetic amylase, (Gamma)-Glutamyltransferase (GGT), Glutamic-oxaloacetic transaminase (GOT), Glutamic-pyruvic transaminase (GPT), bilirubin, hemoglobin, potassium. Additionally or alternatively, the analytes may be substances or combination of substances involved in the intrinsic and/or extrinsic coagulation pathway. Generally, the analyte may be any type of clinical parameter of the body fluid that might be of interest for clinical purposes, such as any type of clinical parameter that might be determined from whole blood. Without restricting further embodiments of the present invention, in the following, in most parts reference will be made to the detection of glucose in whole blood.

The method comprises the following method steps. The method steps may be performed in the given order, i.e. in the order a)-b)-c). However, other orders of the method steps are feasible, such as b)-a)-c). Further, one or more of the method steps may be performed in parallel and/or in a timely overlapping fashion, such as by performing method steps a) and b) at least partially simultaneously and/or by performing method steps b) and c) at least partially simultaneously. Further, one or more of the method steps may be performed repeatedly. Further, additional method steps may be present which are not listed.

The method steps are as follows:

a) performing an optical measurement, wherein at least one test chemical is contacted with the body fluid, wherein the test chemical is an optical test chemical and is adapted to perform at least one detection reaction in the presence of the analyte, wherein at least one optically detectable property of at least one of the body fluid and the test chemical is changed due to the detection reaction, wherein at least one optical measurement value is generated;

b) performing at least one impedance measurement, wherein at least two impedance measurement electrodes are used, wherein at least one alternating electrical signal is applied to the body fluid via the impedance measurement electrodes and wherein at least one answer signal is recorded, wherein at least one impedance measurement value is generated;

c) performing at least one evaluation step, wherein, in the evaluation step, at least one evaluation algorithm is used, wherein the optical measurement value and the impedance measurement value are used for determining a concentration of the analyte in the body fluid.

As used herein, an optical measurement generally is a measurement using at least one optical device and/or using light in at least one of the infrared spectral range, the visible spectral range and the ultraviolet spectral range. Therein, at least one optical measurement value is generated, i.e. at least one measurement value, a plurality of measurement values or, preferably, a series of measurement values, such as a measurement curve.

The test chemical, as used herein, is an arbitrary substance or combination of substances adapted to perform at least one detection reaction in the presence of the analyte. The detection reaction is adapted such that at least one optically detectable property of the body fluid and/or the test chemical is changed due to the detection reaction. Most preferably, the optically detectable property is selected from the group consisting of a fluorescence property and/or a phosphorescence property and/or a reflection property which may be determined by a reflection measurement, such as the measurement of a remission and/or the measurement of a color. Thus, the test chemical is an optical test chemical, such that the at least one optically detectable property of the body fluid and/or the test chemical changes due to the detection reaction.

The test chemical, which is an optical test chemical, generally may be any arbitrary test chemical as known in the art and as e.g. disclosed in one or more of the above-mentioned prior art documents. Additionally or alternatively, other types of test chemicals may be used. In some embodiments, the test chemical comprises at least one enzyme. Especially, the at least one enzyme may comprise at least one of a glucose dehydrogenase and/or a glucose oxidase. Additionally or alternatively, other types of test chemicals and/or components of the test chemical may be comprised, such as one or more co-enzymes and/or one or more mediators.

For test chemicals which may also be used within the present invention, reference may be made to one or more of the test chemicals disclosed above. Thus, as an example, reference may be made to J. Hoenes et al.: The Technology Behind Glucose Meters: Test Strips, Diabetes Technology & Therapeutics, Vol. 10, Supplement 1, 2008, S-10 to S-26. Preferably, one or more optical test chemicals may be employed.

The detection reaction preferably is adapted such that the course and/or the extent of the detection reaction depends on the concentration of the analyte in the body fluid. Thus, as an example, a time development of the at least one optical measurement value and/or the measurement value itself may directly or indirectly provide a measure for the concentration of the analyte in the body fluid. Exemplary embodiments will be given in further detail below.

As used herein, an impedance measurement generally refers to a measurement in which a response or answer of an object or system to an alternating electrical signal is measured, preferably recorded over a period of time and/or over a spectral range or range of frequencies, and, more preferably, evaluated. The alternating electrical signal may be or may comprise an alternating electrical current signal and/or or an alternating voltage signal. Preferably, the alternating electrical signal does not contain any DC component. The term alternating generally refers to the fact that an amplitude and/or phase of the electrical signal changes. Thus, the electrical signal may be a pulsed signal and/or a sinusoidal signal and/or a combination of pulse signals and/or sinusoidal signals. Most preferably, the alternating electrical signal is a sinusoidal signal, i.e. a signal having at least one component having an amplitude and a sine cofactor having a frequency and a phase.

The at least one answer signal generally is an electrical signal which is recorded in response to the application of the alternating electrical signal to the body fluid. The answer signal may be recorded by using the impedance measurement electrodes themselves and/or any other detector, such as one or more additional electrodes. The at least one answer signal preferably is an electrical answer signal. From the at least one answer signal, the at least one impedance measurement value is generated.

Thus, in method steps a) and b), at least one optical measurement value and at least one impedance measurement value, respectively, are generated. In method step a), the at least one optical measurement value may be derived by measuring the at least one optically detectable property, which changes due to the detection reaction. The optical measurement value may be derived from this measurement of the at least one optically detectable property. For this purpose, reference may be made to a large number of known methods and devices for measuring optical properties and deriving at least one optical measurement value thereof. As an example, an end value of an optical measurement curve, such as a remission curve, may be used as an optical measurement value. Thus, as an example, reference may be made to EP 0 821 234 and/or US 2002/0146835 A1. In these documents, means and methods are disclosed for deriving at least one measurement value from a measurement curve, by comparing measurement curves directly or indirectly with one or more thresholds. Thereby, an end point of the detection reaction may be determined. Additionally or alternatively, one or more fitting algorithms are known in the art, in which the measurement curve may be analyzed by using one or more fit functions. Generally, the optical measurement value refers to an arbitrary value, which directly or indirectly, i.e. directly from the optical measurement of the at least one optically detectable property and/or by at least one evaluation algorithm, may be derived from an optical measurement indicating a progress and/or an extent of the detection reaction.

Similarly, the at least one impedance measurement value generally may be or may comprise an arbitrary value or a combination of values which may be derived directly or indirectly from the above-mentioned impedance measurement. As an example, a phase or phase shift of the answer signal, which may also be referred to as the response or response signal, may be recorded. Additionally or alternatively, an amplitude of the answer signal and/or other impedance parameters may be used. Further exemplary embodiments will be given below.

In the at least one evaluation step, at least one evaluation algorithm is used, wherein the at least one optical measurement value and the at least one impedance measurement value are used for determining the concentration of the analyte in the body fluid. As used herein, an evaluation algorithm is an arbitrary algorithm or combination of algorithms, which may comprise one or more algorithm steps, which uses the optical measurement value and the impedance measurement value for determining the concentration. Specifically, the evaluation algorithm may comprise at least one calculation or at least one step implying a calculation algorithm. Thus, as an example, a one-step algorithm may be used which uses both the at least one optical measurement value and the at least one impedance measurement value as input variables of the same equation, thereby calculating the concentration of the analyte in the body fluid. Alternatively, multiple steps may be present, such as a first step using an equation for deriving a rough concentration or estimated concentration of the analyte in the body fluid by using the optical measurement value as an input variable. Subsequently, a correction of the estimated value may be performed by using a second algorithm, which may also be referred to as a correction algorithm and/or which might include at least one correction algorithm, wherein the impedance measurement value is used as an input variable or parameter of the correction algorithm. Further, in a multiple step algorithm or in a combination of algorithms, at least one first step may comprise a failsafe step, using one or both of the impedance measurement value or the optical measurement value as variables, deriving a failsafe result. Further, at least one second step may comprise a calculation or determination of the concentration of the analyte in the body fluid, using one or both of the impedance measurement value or the optical measurement value, such that, in combination of the first step and the second step, both the impedance measurement value and the optical measurement value are used in the algorithm.

Again, additionally or alternatively, other types of multi-step algorithms may be used. Thus, as an example, by using the at least one impedance measurement value, at least one appropriate algorithm for evaluating the optical measurement value and deriving the concentration of the analyte from this optical measurement value may be selected from a plurality of evaluation algorithms. Various possibilities are feasible and will be known to the skilled person. All these possibilities of one step or multiple step algorithms shall be included when referring to the fact that, in the evaluation step the optical measurement value and the impedance measurement value are used for determining the concentration of the analyte in the body fluid.

In step c), the concentration of the analyte of the body fluid may be a corrected concentration which is corrected for at least one interferent concentration in the body fluid. As used herein, the term interferent generally refers to an arbitrary substance or a combination of substances which may influence and/or falsify the determination of the analyte concentration. Thus, specifically, the at least one interferent may be a substance or a combination of substances which influence the course and/or extent of the detection reaction itself and/or which may interfere with the optical measurement and the determination of the at least one optical measurement value. Thus, the at least one interferent may take part in the detection reaction itself, as a partner and/or a catalyst of the detection reaction, and/or the interferent may have an impact on the optical measurement, i.e. may influence the at least one optically detectable property which is measured during the optical measurement and, thus, may falsify the at least one optical measurement value.

The interferent may be selected from the group consisting of: a drug; a disinfectant; a redox reactive substance; ascorbic acid; a peroxide; a glutathione; sodium; a particulate component in the body fluid, preferably at least one cellular component in the body fluid or a hematocrit value. Most preferably, in step c), the concentration of the analyte of the body fluid is a corrected concentration which is corrected for the hematocrit of whole blood. Thus, most preferably, the concentration of the analyte in the body fluid is a corrected glucose concentration in whole blood, which is corrected for the hematocrit of the whole blood. Generally, as used herein, the term hematocrit or hematocrit value may refer to a parameter indicating and/or quantifying a content of cellular components within the body fluid, specifically within whole blood. Thus, the hematocrit or hematocrit value may be a parameter, such as a parameter derived from a measurement, which indicates the content of cellular components within the volume of whole blood, such as a volume content.

Additionally or alternatively, as outlined above, the evaluation algorithm in step c) may comprise at least one failsafe algorithm. As used herein, a failsafe algorithm generally may be an arbitrary algorithm which, such as on the basis of the optical measurement value and/or on the basis of the impedance measurement value, prevents unreasonable results which do not correctly render the actual situation of the body fluid, such as by providing unreasonable concentrations of the analyte in the body fluid. Thus, generally, the failsafe algorithm may be or may comprise an arbitrary algorithm preventing failures of the evaluation step or rendering these failures less probable.

As an example, failures of the determination of the concentration of the analyte in the body fluid may occur due to one or more of the interferent discussed above and/or due to one or more parameters, such as one or more of: an environmental parameter; an experimental parameter; or a sample parameter. Thus, the at least one parameter which may influence a result of the evaluation step and which may give rise to failures may be selected from the group consisting of: a temperature of the sample of the body fluid; a temperature of a test element used for detecting the analyte in the body fluid; a temperature of a measurement system used for detecting the analyte in the body fluid; a degree of wetting of a test chemical and/or a test field of a test element used for detecting the analyte in the body fluid; a degree of filling of a capillary element, specifically of a capillary element of a test element for detecting the analyte in the body fluid; a velocity of wetting of a test chemical and/or a test field of a test element used for detecting the analyte in the body fluid, such as a velocity of filling of a capillary element; an interruption of wetting of a test chemical and/or a test field of a test element used for detecting the analyte in the body fluid by the sample of the body fluid, such as an interruption of filling of a capillary element; a non-uniform wetting of a test chemical and/or a test field of a test element used for detecting the analyte in the body fluid, such as a repeated sample application; a parameter characterizing a timing of wetting of a test chemical and/or a test field of a test element used for detecting the analyte in the body fluid.

The at least one failsafe algorithm specifically may comprise comparing one or both of the optical measurement value or the impedance measurement value with at least one threshold. Thus, as an example, the at least one failsafe algorithm may comprise comparing the optical measurement value and/or the impedance measurement value with one or more out-of-range thresholds indicating that one or more of these measurement values are out of a predetermined range and/or are above an upper limit and/or are below a lower limit. The comparison with the one or more threshold values may be a direct comparison, such as by directly comparing one or both of the measurement values with the at least one threshold. Additionally or alternatively, before comparing one or both of the measurement values with one or more thresholds, one or both measurement values may be transformed into one or more secondary values. Thus, as an example, from the at least one impedance measurement value, at least one secondary impedance measurement value may be derived by at least one impedance evaluation algorithm, such as for the purpose of deriving a hematocrit from the impedance measurement value, as known to the skilled person and as e.g. disclosed in one or more of the prior art documents listed above. Thus, the secondary impedance measurement value may be the hematocrit, which may be compared with one or more threshold levels, such as with one or more out-of-range thresholds. Similarly, additionally or alternatively, specifically by using the impedance measurement value, one or more of the following may be determined as one or more secondary impedance measurement values and may be compared with one or more threshold levels, such as with one or more out of range thresholds: a degree of filling of a capillary element; a degree of wetting of a test chemical and/or a test field; a temperature. Additionally or alternatively, specifically by using the impedance measurement value and/or by using one or more filling electrodes contained within the impedance measurement electrodes, at least one dosing parameter may be determined, the dosing parameter describing a sample application to a test element such as to a capillary element of a test element. The at least one dosing parameter may be used as a secondary impedance measurement value and may be compared with one or more threshold values such as with one or more out of range thresholds. The at least one dosing parameter specifically may be selected from the group consisting of: a dosing parameter characterizing short dosings; a dosing parameter characterizing intermitted dosings; a dosing parameter characterizing double dosings such as a second dosing after the analytical measurement has already started. Thus, for one or more of these parameters, allowable ranges may be predetermined, and the failsafe step may comprise an evaluation regarding the question if one or more of the parameters to be monitored are within their respective allowable ranges.

In the multiple step evaluation algorithm comprising the at least one failsafe step, the evaluation algorithm and/or the overall method may be stopped in case a failure should be detected. Thus, in case the failsafe step should come to the result that one or more intrinsic or extrinsic parameters are out of range, such as one or more of the interferent listed above and/or such as one or more of the parameters listed above, a failure may be recognized, preferably automatically, and the evaluation step may be stopped. The method may be performed fully or partially in an automated fashion, such as by using the measurement system disclosed in further detail below, and a user may be notified that a failure has occurred, optionally including information regarding the type of failure and/or regarding a cause of the failure. Thus, as an example, at least one measurement device may be provided having at least one display element, by which the user may be notified, such as optically.

In case the evaluation step comprises a multiple step algorithm, including at least one failsafe step and at least one determination step, the use of the at least one optical measurement value and of the at least one impedance measurement value may be distributed over a plurality of steps, such that the impedance measurement value and the optical measurement value may be used in different steps. Alternatively, as outlined above, the at least one impedance measurement value and the at least one optical measurement value may be used in one and the same step.

Thus, as an example, solely the at least one impedance measurement value and/or at least one secondary measurement value derived thereof (the latter in the following shall be included by the meaning of using the impedance measurement value) may be used. In case the at least one failsafe step comes to a positive result indicating that no failure has occurred, one or more further steps may be performed, using the optical measurement value only or using a combination of the optical measurement value and the impedance measurement value.

Summarizing the possibilities of using at least one failsafe step within the evaluation step, step c) may comprise at least one failsafe step, wherein, in the failsafe step, one or both of the optical measurement value or the impedance measurement value are used. In an embodiment, only the impedance measurement value may be used in the failsafe step. The failsafe step may comprise comparing at least one of the optical measurement value or the impedance measurement value or one or more secondary measurement values derived thereof (i.e. derived of the optical measurement value, the impedance measurement value or a combination of the optical measurement value and the impedance measurement value) with at least one threshold value, specifically with at least one out-of-range threshold value. The failsafe step may further comprise comparing at least one parameter with at least one threshold value, specifically at least one parameter selected from the group consisting of: an interferent concentration, specifically a hematocrit; an environmental parameter, specifically a temperature of a surrounding environment; an experimental parameter, specifically a degree of filling of a capillary element and/or a degree of wetting of a test chemical; a sample parameter, specifically a sample temperature. These parameters may be measured directly or may be derived as secondary measurement values from one or both of the optical measurement value or the impedance measurement value. The method may be stopped in case, in the failsafe step, a failure is detected.

In case the evaluation step comprises at least one failsafe step, the failsafe step may at least partially be performed before performing further steps, such as before deriving the concentration of the analyte in the body fluid. Additionally or alternatively, the at least one failsafe step may fully or partially be performed at a different point in time, such as fully or partially simultaneously to deriving the concentration of the analyte in the body fluid and/or after deriving the concentration of the analyte in the body fluid. Further, the failsafe step may fully or partially be performed repeatedly.

In case the at least one failsafe step comprises evaluating the at least one impedance measurement, i.e. comprises using the at least one impedance measurement value, such as using the impedance measurement value without using the optical measurement value, the impedance measurement specifically may be adapted to the at least one parameter for which a failure may be detected, such as a filling or wetting parameter, a temperature, a hematocrit or a combination thereof. Thus, as an example, a geometry of the at least two impedance measurement electrodes may be adapted to the failsafe step. As an example, in case a filling or wetting control shall be performed, the at least two impedance measurement electrodes specifically may fully or partially be located in a position in which a complete filling or incomplete filling may be detected, such as at an end of a capillary element. The at least two impedance measurement electrodes may comprise a plurality of electrodes adapted for various purposes, such as for performing or supporting one or more failsafe mechanisms. Thus, the at least two impedance measurement electrodes may comprise one or more electrode pairs for failure detection and/or other purposes. As an example, at least one first pair may be provided for dose detection, such as at an entry of a capillary channel of a test element. Additionally or alternatively, at least one second electrode pair may be provided for detecting one or more interferents, such as for hematocrit detection, preferably at the location of at least one test chemical for detecting the analyte, such as within or close to a test field comprising the at least one test chemical. Again, additionally or alternatively, at least one third electrode pair may be provided for measurement of temperature influences and/or conductivity influences, wherein the third electrode pair preferably is also located at the location of at least one test chemical for detecting the analyte such as within or close to a test field comprising the at least one test chemical. Further, additionally or alternatively, at least one fourth electrode pair may be provided for wetting control, such as in a position which allows for detecting whether a sample has passed a test chemical such as a test field comprising the at least one test chemical. As an example, the fourth electrode pair may be located downstream the test chemical in a capillary element such that, by using the fourth electrode pair, a wetting of the test chemical may be detected.

As outlined above, the evaluation algorithm of step c) may be a single step evaluation algorithm or may comprise a plurality of steps or substeps. Thus, as an example, step c) may comprise the following substeps:

c.1) determining an estimated value of the concentration of the analyte in the body fluid by using the optical measurement value and a first evaluation algorithm;

c.2) determining a corrected value of the concentration of the analyte in the body fluid by using the estimated value and correcting the estimated value by using at least one correction algorithm, wherein the correction algorithm uses the impedance measurement value.

Thus, as an example, an estimated value of the analyte concentration may be determined by using a known relationship between the at least one optical measurement value and the analyte concentration. These correlations may be determined empirically, analytically or semi-empirically. Thus, as an example, the first evaluation algorithm may comprise a known correlation between an end value of a remission curve measured during the detection reaction, such as an end value determined by one or more of the algorithms disclosed in the prior art documents cited above, and a glucose concentration. The correction algorithm which is used in step c.2) may comprise an arbitrary correction algorithm correcting for the impedance measurement value, such as in order to correct the estimated value of the concentration of the analyte for at least one interferent concentration, such as for hematocrit. Thus, in step c.1), by using the first evaluation algorithm, an estimated value of a glucose concentration in whole blood may be generated which, in step c.2), may be corrected for an actual value of the hematocrit. Other embodiments are feasible.

The correction algorithm may, for example, comprise an application of a correction factor and/or an offset. Other correction algorithms are feasible. Further, other types of corrections may be applied, such as an application of a correction factor which may be derived from a correction curve indicating the correction factor as a function of the impedance measurement value and/or an interferent concentration determined thereof, such as hematocrit. Further details will be given below.

Further embodiments of the present invention refer to the measurement setup used for performing the method or used during the method. Thus, a single test element may be used for both method step a) and method step b). Thus, the test element may both comprise the at least one test chemical, such as at least one test field comprising the at least one test chemical, and the at least two impedance measurement electrodes.

The test element may comprise a substrate and the at least two impedance measurement electrodes applied to the substrate. The test element may further comprise at least one test field connected to the substrate, such as applied to a surface of the substrate and/or integrated into the substrate, wherein the test field comprises the at least one test chemical. Therein, one single test field having one test chemistry may be applied and/or a plurality of test fields having the same test chemistry and/or different types of test chemistry may be used.

The test field may be spatially separated from the impedance measurement electrodes. Thus, the test field may not contact the impedance measurement electrodes. As an example, the impedance measurement electrodes may be applied to the substrate in one region of the substrate, whereas the at least one test field may be applied to the substrate in a different region of the substrate.

The test element may additionally comprise at least one application location, where a sample of the body fluid is applied to. Consequently, the at least one application location may be a location in which a sample of the body fluid is applicable to the test element. Thus, when referring to the body fluid in the method disclosed above and/or as disclosed in further details below, the at least one sample of the body fluid may be used as a representative amount of the body fluid and, thus, as the body fluid itself.

One or more application locations may be provided. In a specific embodiment, the at least one application location and/or the test element are designed such that one and the same sample of the body fluid is supplied both to the test chemical and to the at least two impedance measurement electrodes. Thus, as an example, the test element may comprise at least one capillary element, wherein the capillary element may be adapted to conduct the sample of the body fluid or at least a part of the sample of the body fluid from the application location to at least one of the test chemical and the impedance measurement electrodes, preferably to both the test chemical and the impedance measurement electrodes.

Further embodiments refer to the material of the impedance measurement electrodes or to the material of at least one of the at least two impedance measurement electrodes. Thus, preferably, at least one impedance measurement electrode out of the at least two impedance measurement electrodes comprises a metal selected from the group consisting of: aluminum, molybdenum, tungsten, tantalum, niobium, zirconium, titanium, ruthenium, rhodium, iridium, palladium, platinum, silver, gold. As will be outlined in further detail below, aluminum is specifically preferred. Still, additionally or alternatively, one or more metal selected from the group of molybdenum, tungsten, tantalum, niobium, zirconium, titanium may be used with similar advantages. Additionally or alternatively, one or more of the metals selected from the group consisting of ruthenium, rhodium, iridium, palladium, platinum, silver and gold may be used, however, with some disadvantages, as will be outlined in further detail below.

Preferably both of the impedance measurement electrodes or, in case more than two impedance measurement electrodes are provided, preferably all of the impedance measurement electrodes comprise the metal selected from the named list of metals. Most preferably, aluminum is used. The named metals may be present in a pure form, such as by using pure metals. Alternatively, one or more of the named metals may be present in the form of at least one alloy. Again, additionally or alternatively, one or more of the named metals may be used in an oxide form. Other chemical compounds comprising one or more of the named metals are feasible.

In case one or more of the impedance measurement electrodes comprise an alloy comprising one or more of the named metals aluminum, molybdenum, tungsten, tantalum, niobium, zirconium, titanium, ruthenium, rhodium, iridium, palladium, platinum, silver and gold, one or more additional elements, preferably metals, may be present as additive components in the alloy. As an example, one or more elements selected from the following group may be present as additive components in the alloy:

Lithium (Li), Sodium (Na), Potassium (K),
Beryllium (Be), Magnesium (Mg), Calcium (Ca), Strontium (Sr), Scandium (Sc), Yttrium (Y),
Titanium (Ti), Zirconium (Zr), Hafnium (Hf),
Vanadium (V), Niobium (Nb), Tantalum (Ta),
Chromium (Cr), Molybdenum (Mo), Tungsten (W),
Manganese (Mn), Rhenium (Re),
Iron (Fe), Ruthenium (Ru), Cobalt (Co), Rhodium (Rh), Iridium (Ir),
Nickel (Ni), Palladium (Pd), Platinum (Pt),
Copper (Cu), Silver (Ag), Gold (Au),
Zinc (Zn), Boron (B), Indium (In),
Silicon (Si), Germanium (Ge),
Tin (Sn), Lead (Pb),
Antimony (Sb), Bismuth (Bi),
Selenium (Se), Tellurium (Te),
Lanthanum (La), Cerium (Ce), Praseodymium (Pr), Neodymium (Nd), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu).

Thus, besides one or more metals selected from the group consisting of aluminum, molybdenum, tungsten, tantalum, niobium, zirconium, titanium, ruthenium, rhodium, iridium, palladium, platinum, silver, gold, the alloy may comprise one or more of the above-mentioned additives. Additionally or alternatively, one or more other metallic or nonmetallic additives may be present.

Preferably, the impedance measurement electrodes are bare metal electrodes. Thus, as an example, the impedance measurement electrodes are not covered by any type of test chemical which is adapted to perform a chemical reaction with the body fluid and/or the analyte. Thus, the bare metal electrodes are in direct contact with the body fluid during the impedance measurement. As will be outlined in further detail below, the term "bare", however, shall not preclude the possibility that an oxide layer of the metal of the metal electrodes may form at a surface of the metal electrodes. Thus, as an example, natural metal oxide layers may form on the surface of many metals, such as on an aluminum surface. Still, since no additional layers are applied to the metal electrodes intentionally and since the metal electrodes are still in contact with the body fluid during the impedance measurement, these metal electrodes having a thin oxidic layer formed on the respective surfaces shall still be comprised within the meaning of bare metal electrodes. Specifically, in case the metal electrodes comprise aluminum or an alloy thereof, the formation of a natural oxidic layer of aluminum oxide on the surface of the respective metal electrode shall still be comprised within the meaning of a bare metal electrode.

The impedance measurement, as outlined above, may imply an application of a sinusoidal signal. The impedance measurement may imply at least one of: an application of a sinusoidal voltage to the impedance measurement electrodes and a measurement of an electrical current through the impedance measurement electrodes as an answer signal, preferably for a plurality of frequencies; an application of a sinusoidal electrical current to the impedance measurement electrodes, i.e. through the impedance measurement electrodes, and a measurement of a voltage required to obtain the electrical current, wherein the voltage forms the answer signal or a part of the answer signal, preferably for a plurality of frequencies. Thus, generally, the impedance measurement may comprise a current-voltage-measurement and/or a voltage-current-measurement. Appropriate impedance measurement devices and/or impedance analyzers are known in the art and are commercially available.

Preferably, the impedance measurement is performed for a plurality of frequencies, such as over a band of frequencies. As an example, frequencies in the range of 10 Hz to 1000 kHz, preferably in the range of 100 Hz to 400 kHz, may be used. Thus, the at least one impedance measurement may imply the measurement of a spectrum of at least one answer signal and/or at least one impedance measurement value over a frequency range, such as a frequency range within the above-mentioned range.

The impedance measurement generally may imply a measurement of one or more impedance measurement values, which may be derived from one or more parameters of the sample determined during the impedance measurement.

Since impedance measurements are widely known in the art, the skilled person immediately will recognize impedance measurement values which may be used in the present application. As an example, the impedance measurement may imply a measurement of at least one of the following parameters of the sample: a conductivity, preferably a complex electrical conductivity; an admittance; a phase shift, such as a phase shift between an electrical current signal and a voltage answer signal and/or a phase shift between a voltage signal and an electrical current answer signal; a permittivity; an impedance, preferably a complex impedance; a real part (related to admittance or impedance); an imaginary part (related to admittance or impedance).

The at least one impedance measurement value may be formed by one or more of the above-mentioned parameters or may comprise one or more of the above-mentioned parameters. Additionally or alternatively, the at least one impedance measurement value may be at least one secondary value which may be derived by one or more of the above-mentioned parameters. Thus, as an example for the latter option, a hematocrit value may be derived from an admittance and/or a phase, by using a known relationship between the admittance and/or the phase and the hematocrit value. In this case, the admittance and/or phase and/or the hematocrit value derived thereof may be used in the at least one evaluation algorithm, such as in the at least one correction algorithm, such as for correcting an estimated value of a glucose concentration in whole blood for an actual value of the hematocrit. Various other embodiments are feasible.

In a further aspect of the present invention, a test element for detecting at least one analyte in a body fluid is disclosed.

As used herein, a test element is an arbitrary device which may be used for qualitatively and/or quantitatively detecting the at least one analyte in the body fluid.

The test element comprises:
a) at least one test chemical which may be contacted with the body fluid, the test chemical being an optical test chemical and being adapted to perform at least one detection reaction in the presence of the analyte, wherein at least one optically detectable parameter of at least one of the body fluid and the test chemical is changed due to the detection reaction;
b) at least two impedance measurement electrodes adapted for applying an alternating electrical signal to the body fluid and adapted to record at least one answer signal.

The test element may further comprise one or more contact pads for electrically contacting the at least two impedance measurement electrodes. Further, the test element may comprise two or more contact leads, such as contact leads leading from the contact pads to the respective impedance measurement electrodes.

As outlined above, the at least one test chemical preferably forms at least one test field and/or is part of at least one test field. The test field may comprise a single-layer setup, comprising only one detection layer comprising the test chemical. Alternatively, the test field may have a multi-layer setup of at least two layers, wherein at least one detection layer comprising the at least one test chemical may be combined with one or more additional layers, such as one or more spreading layers and/or one or more separation layers and/or one or more pigment layers for providing an optical background, such as a white background, for improved optical measurements. Multi-layer setups of this type are known in the art. Thus, as an example, the test field may comprise at least one detection layer and, additionally, at least one separation layer (e.g. for separating blood cells) and/or optical layer comprising one or more pigments, such as one or more inorganic pigments, such as one or more metal oxides, preferably titanium dioxide.

The test element may be adapted for use in the method according to one or more of the embodiments disclosed above and/or according to one or more of the embodiments disclosed in further detail below. Thus, for potential details of the test element, reference may be made to the disclosure of the method.

As outlined above, the at least two impedance measurement electrodes preferably may comprise a metal selected from the group consisting of: aluminum, molybdenum, tungsten, tantalum, niobium, zirconium, titanium, ruthenium, rhodium, iridium, palladium, platinum, silver, gold. One or more of these metals may be present in a pure form and/or as an alloy or oxide. Additionally or alternatively, one or more additives may be present, specifically in an alloy. For further details, reference may be made to the disclosure of the electrode materials above. Preferably, the impedance measurement electrodes are bare metal electrodes. Preferably, the impedance measurement electrodes are in direct contact with the body fluid during the impedance measurement.

As an example, the at least two impedance measurement electrodes may be made of uncoated aluminum. All parts of aluminum which may get in contact with the body fluid preferably do not react with any electro-active substance of the sample. Thus, for bare aluminum electrodes, this type of electrodes generally fulfills these requirements, since bare aluminum is generally covered by a naturally grown isolating oxide layer. By passivation of the aluminum surface by an oxide layer, and oxidation or reduction of redox-reactive substances within the electrolyte, such as a blood sample or parts thereof, typically is not possible, since the oxide layer widely prevents an electron transfer, at least within a typically used range of potentials. In case a sufficient voltage, such as a DC voltage, is applied, an anodically polarized thin-film aluminum electrode typically is completely oxidized, until no electrical conductivity remains. Impedance measurements at aluminum electrodes typically are not influenced by electro-active drugs in a wide frequency range in aqueous solutions. Impedance measurements using aluminum electrodes may be performed from low frequencies of about 100 Hz to higher values of around 100 kHz. Impedance spectra typically show a selective sensitivity towards temperature, hematocrit and salt concentration of whole blood samples.

Additionally or alternatively, the at least two impedance measurement electrodes may fully or partially be structured or patterned. Thus, as an example, the at least two impedance measurement electrodes, as outlined in detail above, may contain one or more electrode pairs which may be adapted, by appropriate patterning, for various purposes. Thus, one or more of the following electrode pairs having appropriate patterning may be provided:
  at least one first pair for dose detection, such as at an entry of a capillary channel of a test element;
  at least one second electrode pair for detecting one or more interferents, such as for hematocrit detection, preferably at the location of at least one test chemical for detecting the analyte, such as within or close to a test field comprising the at least one test chemical;
  at least one third electrode pair for measurement of temperature influences and/or conductivity influences, wherein the third electrode pair preferably is located at the location of at least one test chemical for detecting the analyte such as within or close to a test field comprising the at least one test chemical;

at least one fourth electrode pair for wetting control, such as in a position which allows for detecting whether a sample has passed a test chemical such as a test field comprising the at least one test chemical, such as a fourth electrode pair being located downstream the test chemical in a capillary element such that, by using the fourth electrode pair, a wetting of the test chemical may be detected.

Therein, the arbitrary nomenclature "first", "second", "third" and "fourth" is used without ranking and without restricting the possibility of using arbitrary combinations of these electrode pairs, such as a third electrode pair and a fourth electrode pair, without using a first and second electrode pair. Further, in case a plurality of electrode passes provided, two or more of the electrode pairs may partially be combined, such as by using at least one common electrode shared by two or more electrode pairs.

In case the at least one impedance measurement electrode comprises a plurality of electrode pairs, a geometry and/or structuring and/or patterning of the electrode pairs may be adapted to their respective purpose. Specifically, at least one cell constant of at least one impedance measurement electrode pair or, specifically, the different cell constants of a plurality of electrode pairs of the impedance measurement electrodes may be adapted to their respective purpose. As generally known to the skilled person, the cell constant Z of an arbitrary conductor, such as of an electrode pair, generally denotes a correlation between a resistance R of the conductor and the specific conductivity $\rho$: $R = \rho \cdot Z$. For exemplary embodiments of electrode patterning adapted to various purposes, such as micro-electrode structures on macro-electrode structures having various cell constants, reference may be made to WO 2004/113910 A1 as discussed above. Thus, different structures of impedance measurement electrodes such as aluminum electrodes may be used, having significantly differing cell constants. In that way, temperature effects may efficiently be separated from interferences of hematocrit and sodium chloride recording phase shift and admittance over wide frequency spectra.

Additionally, as outlined above, the at least two impedance measurement electrodes and/or further electrodes may be used for monitoring a filling process of a capillary element, such as a capillary element of a test element such as a test strip. Thus, as an example, a special small bar structure of aluminum electrodes which may be placed in the center of the lower edge of an optional capillary element (i.e. located downstream of the test chemical in a capillary element), as fill end electrode, for detecting the filling behavior of the test strip. Using the same electrode as impedance electrode, the structuring may be designed such that impedance data are independent from the width of the capillary. Another electrode pair made of aluminum may be placed at the upper edge of the capillary in an orthogonal direction to the capillary (i.e. located upstream of the test chemical in a capillary element). Impedance measurements of this electrode pair can be used as dose detect signals and can be used in order to detect the influence of temperature, hematocrit or sodium chloride. Therein, sodium chloride may generally be replaced by an ionic strength, as a general classification, since sodium ions are simply an example of ions. Impedance measurement electrodes used for filling detection may be used for ensuring that a test chemical and/or other impedance measurement electrodes used for other purposes such as for detecting one or more parameters of the sample are fully covered by the sample. Thereby, a partial covering may be detected and/or avoided. A partially covering by the sample of the body fluid may change a cell constant of the impedance measurement electrodes, because the sample covered portion of the conductive surface within the sample compartment is a major component of the cell constant calculation term. Thus, as outlined above, the impedance measurement electrodes may comprise two or more electrode pairs, for different purposes. A common use of one electrode pair for more than one purpose is generally possible, and may, however, induce technical challenges. Still, in order to combine electrode contacts and in order to reduce the overall number of electrode contacts, combining several purposes within one electrode pair may be beneficial.

The test element generally may have an arbitrary form or format, such as one or more of the test element formats known in the art. As an example, the test element may be selected from the group consisting of: a test strip, a test tape, a test disc, a test cartridge. However, additionally or alternatively, other types of test elements may be used.

As outlined above, the test element preferably may comprise at least one substrate and the at least two impedance measurement electrodes applied to the substrate. The test element may further comprise at least one test field connected to the substrate, wherein the test field comprises the test chemical. The test field may be applied to an outer surface of the substrate and/or may be integrated into the substrate, such as by applying the at least one test field to an interior surface of the substrate.

The substrate may comprise a single layer setup or may comprise a multi-layer setup. Thus, the substrate may comprise one or more of a paper material, a plastic material, preferably a foil, a metal and a ceramic material. Further, combinations of materials are feasible. The substrate may comprise a multi-layer setup, such as by using a laminate. Further, the substrate may comprise one or more fluidic structures, such as one or more capillary elements. For this purpose, two or more substrates may be provided, wherein a channel is disposed in between the substrate, such as by separating the substrate by one or more spacers. Additionally or alternatively, one or more fluidic structures on a surface of the substrate may be provided, such as by using one or more open capillary channels, such as one or more capillary slits. Various embodiments are feasible and, generally, are known in the art.

In a specific embodiment, as outlined above, the test field is spatially separated from the impedance measurement electrodes. Thus, preferably, the impedance measurement electrodes are not in contact with the at least one test chemical. As outlined above, the impedance measurement electrodes preferably are bare metal electrodes which are in direct contact with the body fluid during the impedance measurement.

As further outlined above, the test element may comprise at least one application location, where the sample of the body fluid is applicable to. The application location may be in direct contact with the at least one test chemical and/or the at least two impedance measurement electrodes. Alternatively, one or more transfer elements may be provided for transferring the sample of the body fluid from the application location to one or both of the test chemical and the impedance measurement electrodes. Thus, as an example, the test element may comprise at least one capillary element, which is adapted for conducting the sample of the body fluid from the application location to at least one, preferably both, of the test chemical and the impedance measurement electrodes. As outlined above, the at least one capillary element may comprise at least one of a closed capillary and an open capillary, such as a capillary slit.

Further embodiments refer to the test element and the at least one optically detectable property. Thus, as outlined above, the optical property generally may be an arbitrary optical property which changes due to the detection reaction and, the measurement of which, may therefore provide at least one item of information regarding a progress, an extent or a status of the detection reaction. Most preferably, the at least one optically detectable property is selected from the group consisting of a color; a reflection property such as a remission and a fluorescence of the test chemical. Other embodiments are feasible.

Thus, generally, the test element according to the present invention may be a hybrid test element, comprising both the at least two impedance measurement electrodes and the optical test chemical adapted for performing optical detections of the analyte in the body fluid. Preferably, the test element is a hybrid test strip, comprising both the optical test chemical and the impedance measurement electrodes, thereby allowing for combined impedance and optical measurements with one and the same test strip.

In a further aspect of the present invention, a measurement system for detecting at least one analyte in a body fluid is disclosed. As used herein, a measurement system is a device or a combination of a plurality of interacting devices adapted for performing one or more measurements, specifically for detecting the at least one analyte and, more specifically, for measuring a concentration of the at least one analyte. The measurement system may be embodied as a single device or as a plurality of interacting devices.

The measurement system comprises:
i) at least one test element according to the present invention, such as at least one test element or a plurality of test elements as disclosed above or as disclosed in further detail below;
ii) at least one measurement device adapted for using the test element, wherein the measurement device is adapted to perform the method according to the present invention, such as the method according to one or more of the embodiments disclosed above or one or more of the embodiments disclosed in further detail below.

In order to use the test element, i.e. to perform at least one optical measurement and at least one impedance measurement by using the test element, the measurement system may comprise one or more appropriate devices or components. Thus, firstly, the measurement device may comprise at least one test element receptacle adapted for receiving the test element. The geometric shape and/or details of the test element receptacle may depend on the nature of the test element itself. Thus, in case the test element is a test strip, the test element receptacle may comprise at least one slot adapted for receiving the test strip. In case the test element comprises a test tape, the test element receptacle may comprise a tape magazine. Other embodiments of the test element receptacle will be obvious to the skilled person in view of the aforementioned details of potential embodiments of the test strip.

The measurement device may further comprise at least one optical detector which is adapted to measure the at least one optically detectable property and to generate the at least one optical measurement value. Thus, as an example, the detector may comprise at least one light source for illuminating at least one part of the test chemical, such as for illuminating at least part of a test field comprising the test chemical. The detector may further comprise at least one light-sensitive element for detecting light propagating from the test chemical to the detector. As an example, the light source may comprise one or more of a light-emitting diode, a laser diode, another type of laser, an incandescent light or a light bulb or any other type of light source for illuminating at least part of the test chemical with light. Additionally or alternatively, ambient light can be used to illuminate at least part of a test field comprising the test chemical. Therein, light having one or more wavelengths may be used. Thus, the optical measurement may be performed in one or more wavelength ranges, by using one or more light sources having the same or different spectral properties.

The light-sensitive element may generally comprise an arbitrary element which is adapted to generate at least one electrical signal in response to an illumination of the light-sensitive element. This electrical signal, which may be or may comprise a current signal and/or a voltage signal, may directly or indirectly be used for generating the at least one optical measurement value. Thus, the at least one electrical signal generated by the at least one light-sensitive element may directly be used as the at least one optical measurement value or may be transformed into the at least one optical measurement value. Thus, as outlined above, a plurality of optical measurement values may be evaluated in order to derive at least one end value as a new optical measurement value. Other options are feasible.

In a specific embodiment, the detector is adapted to perform at least one remission measurement, by illuminating the test chemical, preferably the test field, with light and by detecting light reflected and/or scattered from the test chemical. Therein, light in one or more of the visible spectral range, the infrared spectral range and the ultraviolet spectral range may be used. By performing remission measurements, which are well-known to the skilled person, color changes in the test chemical which may occur due to a progress of the detection reaction may be detected.

The at least one light-sensitive element may comprise an arbitrary organic or inorganic light-sensitive element or an arbitrary combination of light-sensitive elements. Thus, as an example, one or more photodiodes and/or one or more CCD or CMOS chips may be used. Other light-sensitive elements are feasible.

The measurement device may further comprise at least one impedance measurement device, which is connectable to the impedance measurement electrodes and which is adapted to perform the impedance measurements. For the purpose of connecting the impedance measurement device, one or more contacting elements may be provided, such as one or more contacting elements for making electrical contact to one or more contact pads on the test element, wherein the contact pads are connected to the impedance measurement electrodes. As an example, the measurement device may provide one or more contact pins and/or contact springs and/or contact clamps.

The impedance measurement device generally may be or may comprise an arbitrary device known to the skilled person adapted to perform impedance measurements. The impedance measurement device may comprise at least one alternating voltage source, wherein the alternating voltage source is adapted to apply at least one alternating voltage signal to the body fluid via the impedance measurement electrodes, and at least one current measurement device, wherein the current measurement device is adapted to measure at least one electrical current through the at least one impedance measurement electrode. In a specific embodiment, both an amplitude and a phase of the alternating voltage signal may be adjusted by the alternating voltage source. Consequently, preferably, the current measurement device may be adapted to measure the at least one electrical current in both an amplitude-sensitive way and a phase-sensitive way.

The alternating voltage source may be adapted to generate alternating voltage signals at a plurality of frequencies, preferably over a frequency range. Thus, generally, for preferred frequency ranges, reference may be made to the above-mentioned frequency ranges. The current measurement device may be adapted to measure the electrical current in a phase-sensitive way.

Additionally or alternatively to the above-mentioned current-voltage-measurement setup, the impedance measurement device may be adapted to perform voltage-current-measurements. Thus, the impedance measurement device may, additionally or alternatively, comprise at least one alternating current source, which is adapted to induce at least one alternating electrical current through the body fluid via at least one of the impedance measurement electrodes, preferably via the at least two impedance measurement electrodes, and at least one voltage measurement device which is adapted to measure at least one voltage required to induce the alternating electrical current. Again, similarly to the optional alternating voltage source mentioned above, preferably, the alternating current source is adapted to adjust both an amplitude and a phase of the alternating electrical current. Similarly, preferably, the at least one voltage measurement device preferably is adapted to measure the at least one voltage in an amplitude-sensitive way and in a phase-sensitive way. Again, preferably, the alternating current source is adapted to induce alternating electrical currents at a plurality of frequencies, preferably over a frequency range. Again, reference may be made to the preferred frequency ranges listed above.

As outlined above, the voltage measurement device preferably may be adapted to measure the voltage in a phase-sensitive way. Thus, as an example, the voltage may be recorded over at least one measurement resistor, preferably a resistor having a high ohmic resistance. Additionally or alternatively, an amplifier may be used. Generally, voltage sources, current sources, voltage measurement devices and current measurement devices which may be used in the present invention are known to the skilled person and are commercially available, preferably in the field of impedance measurements.

The measurement system may further comprise at least one evaluation unit. The evaluation unit may be adapted to determine the concentration of the analyte in the body fluid by performing the at least one evaluation algorithm, by using the at least one optical measurement value and the at least one impedance measurement value. For this purpose, the at least one evaluation unit, which may be embodied as a single unit or which may comprise one or more interacting components, may comprise one or more data-processing devices. The one or more data-processing devices may be or may comprise one or more microcomputers and/or other types of computers. Thus, as an example, a microprocessor may be integrated into a hand-held device. Additionally or alternatively, external data-processing devices may be included into the measurement device, such as one or more personal computers, one or more computer networks or one or more other types of data processing devices.

Thus, generally, the measurement device may be embodied as a single component device which may be handled in one piece. Alternatively, the measurement device may comprise multiple components which may be handled independently, such as a measurement unit comprising the optical detector and the impedance measurement device, and at least one evaluation device comprising the at least one evaluation unit and/or parts thereof.

Most preferably, the measurement device is embodied as a hand-held device, i.e. as a device which may be carried by a user and, preferably, which may be transported in a pocket of the user. Alternatively, however, the measurement device may be embodied in a different way, such as by using a table-top or other type of stationary measurement device, which may often be found in analytical laboratories and/or hospitals. Thus, generally, the measurement device may be adapted for use in home monitoring or may be adapted for use in hospitals and/or laboratories.

In a further aspect of the present invention, a use of an impedance measurement for correcting an estimated value of a concentration of an analyte in a body fluid for at least one concentration of at least one interferent is disclosed. For potential interferents, for which the correction may be made, reference may be made to the above-mentioned method and the devices according to the present invention. For the impedance measurement, one or more impedance measurement electrodes may be used, wherein at least one of the impedance measurement electrodes may comprise a metal selected from the group consisting of: aluminum, molybdenum, tungsten, tantalum, niobium, zirconium, titanium, ruthenium, rhodium, iridium, palladium, platinum, silver, gold. For potential details of these metals and the form of the impedance measurement electrodes, reference may be made to the disclosure above, specifically with regards to potential alloys and/or additives.

Further, the estimated value of the concentration of the analyte may be determined by generating at least one measurement value of at least one optically detectable property of at least one optical test chemical. The optical test chemical may be adapted to perform at least one detection reaction in the presence of the analyte, thereby changing the at least one optically detectable property. For further details, reference may be made to the disclosure above.

The impedance measurement and a determination of the estimated value of the concentration of the analyte preferably may be performed by using the same test element. Thus, reference may be made to the disclosure of the test element according to the present invention as provided above.

In a further aspect of the present invention, a use of a metal as an electrode material for electrodes performing impedance measurements in a body fluid is disclosed, wherein the metal is selected from the group consisting of: aluminum, molybdenum, tungsten, tantalum, niobium, zirconium, titanium, ruthenium, rhodium, iridium, palladium, platinum, silver, gold. Again, for optional details of this use, specifically with regard to alloys and/or additives, reference may be made to the impedance measurement electrodes disclosed above. Again, as an example, the metal may be present in a pure form and/or may be used as a metal in a metal alloy and/or may be present in a chemical compound, preferably an oxide. Thus, preferably, aluminum is used in a pure form, as an aluminum alloy or as aluminum oxide. Most preferably, in the use, a concentration of at least one interferent in the body fluid is determined, preferably by using the impedance measurements.

The method, the test element, the measurement system and the uses according to the present invention provide a large number of advantages over known methods and devices. Thus, as outlined above, by using the present invention, the above-mentioned problem of one or more interferents having an influence on the determination of an analyte concentration may be addressed. Specifically, the hematocrit may be corrected for, which may have an influence on the determination of the analyte concentration, such as the blood glucose concentration, in various ways. Thus, the hematocrit may influence a wetting of the test chemical, a solution behavior of reactive components and a transport of components by diffusion from the test chemical into the sample or vice versa. Generally, as will be explained in further detail below, in samples having a high hematocrit, a dye is formed more slowly through the optical detection reaction. The present invention provides means and methods for reliably determining the analyte concentration, independent from a concentration of the one or more interferents. This is simply due to the fact that an optical measurement is combined with an impedance measurement. The impedance measurement may use an alternating voltage and/or an alternating current, and impedance measurement results are strongly related to the presence and/or concentration of interferents and may be used for correcting the analyte measurements. Thus, the impedance measurement may comprise a simple measurement of a conductivity.

Hybrid test strips according to the present invention may be a combination of optical detection test strips with two or more impedance measurement electrodes. The analyte concentration may be determined by optical measurements, such as by photometric measurements, wherein the influence of one or more interferents, such as redox reactive pharmaceuticals, may be excluded and/or diminished.

The two or more impedance measurement electrodes may easily be combined with known capillary elements. Thus, one or more capillary elements may be provided in the test element, wherein the impedance measurement electrodes, which might provide one pair of impedance measurement electrodes or a plurality of pairs of impedance measurement electrodes, may be disposed along a direction of flow of the capillary element. Additionally, by using these impedance measurement electrodes and/or additional electrodes, a filling of the capillary element may be monitored, in order to synchronize the chemical reaction with the detection. Thus, the at least two impedance measurement electrodes or, additionally or alternatively, additional electrodes may be used for sample detection and/or filling detection by the method and/or the measurement system according to the present invention.

The hybrid technology, using hybrid test elements having at least one optical test chemical and at least two impedance measurement electrodes, further may provide advantages with regard to manufacturing. Thus, the test chemical may be coated onto a substrate in broad stripes, which may extend over the full width of the test elements. Thereby, a high cost-efficiency in high throughput methods of manufacturing may be provided. A plurality of test strips may be manufactured simultaneously and may be cut by using appropriate cutting instruments, such as cutting rolls. A calibration effort may be diminished. Further, as opposed to electrochemical test elements, a coating of the impedance measurement electrodes is not necessary. Thus, bare metal impedance measurement electrodes may be used which may remain uncoated. Consequently, manufacturing effects such as shrinking of electrode layers during drying processes may be eliminated.

Summarizing, test elements having a high degree of precision and robustness against interferents and which may provide a high precision measurement result may be used. By simplifying manufacturing and the possibility of using non-noble metals, such as aluminum, manufacturing costs may further be reduced. By applying at least one parameter-specific optical layer, such as at least one test field comprising the at least one test chemical, the hybrid test element may be easily adapted for a plurality of different parameters.

Further, the impedance measurement itself may be used for performing a filling control of at least one capillary element and/or a wetting control of at least one test chemical. As outlined above, the wetting controller may be part of a failsafe step or may form an independent step. Thus, besides providing the at least one impedance measurement value used for determining the concentration of the analyte in the body fluid, the at least two impedance measurement electrodes may further, by the method and the devices according to the present invention, be used for providing at least one wetting information, wherein the wetting information comprises at least one item of information regarding a wetting of at least one of the test element, a capillary element of the test element, the test chemical and the impedance measurement electrodes with the body fluid. Thus, at least one filling information of a capillary element may be generated. Consequently, the method and the measurement system according to the present invention may be adapted to synchronize the impedance measurement and/or the optical measurement with a wetting of the test element with the body fluid. Thereby, an increased precision of the measurement values may be provided.

Further, as outlined above, one or more failsafe mechanisms may be integrated into the method and devices according to the present invention. Thus, as discussed in great detail above, the at least one evaluation step may comprise one or more failsafe steps. Thus, as an example, the method and/or the measurement system according to the present invention may be adapted to detect at least one of:

an incomplete and/or too slow wetting, e.g. an incomplete or too slow filling of at least one capillary element and/or an incomplete or too slow wetting of at least one test chemical, such as at least one test field;

manufacturing or quality problems of the test element, such as an incomplete adhesion of various layers of the test element and/or a migration of adhesive into a capillary channel;

deviations from a predefined temperature range;

a defective test element;

an unwanted change of a geometry of a test element and/or an unwanted change of a cell constant of at least one electrode pair of impedance measurement electrodes.

For further details of the failsafe step and for potential out-of-range detection of one or more parameters, reference may be made to the disclosure of the failsafe step given above. Further, reference may be made to the failsafe mechanisms as disclosed in the above-mentioned US 2007/0102292 A1. These failsafe algorithms may also be used in the context of the present invention. Still, other failsafe mechanisms are feasible.

The results of the impedance measurement may be influenced e.g. by the hematocrit and/or the temperature. Still, as will be shown in further detail below, impedance measurements generally are not influenced by the concentration of the analyte itself. By providing additional impedance measurement information, estimated values of the analyte concentration, such as estimated glucose concentrations, may be corrected and/or an evaluation algorithm may be adapted.

As outlined above, for the impedance measurement electrodes, electrodes made of aluminum or comprising aluminum and/or made of one or more of the other metals listed above may be used. Thereby, a cost-efficient test element combining an optical detection and, additionally, combining the advantages of integrated electrical conductive structures, may be manufactured.

For the hybrid test elements, a coating technology typically used in photometric systems may be applied. Since these manufacturing technologies generally have been optimized for high throughputs and low calibration effort, the manufacturing costs may generally be lowered.

For the hybrid test element, the electrodes preferably remain uncoated. Consequently, as outlined above, a shrinking of a coating, such as a shrinking of a foil, during drying processes may be avoided.

Further, hybrid test strips having an optical detection, such as a photometric detection, as well as impedance measurements using e.g. aluminum electrodes, may be combined with one or more test chemicals known in the art, such as with the above-mentioned cNAD test chemical. Hybrid test strips having aluminum electrodes and the cNAD test chemical do not exhibit any interferences with redox reactive pharmaceuticals such as ascorbic acid and/or glutathione. A passivating oxide layer, which may be present on aluminum electrodes, may provide a high resistance of these electrodes against corrosion. For impedance measurements, the impedance measurement electrodes therefore preferably are uncoated and are not coated by any chemical process. Contrarily, gold surfaces have to be protected against formation of oxides. Further, in contrast to manufacturing processes for gold or palladium electrodes, no cleaning step by plasma cleaning is required.

The hybrid test element may also be applied for other analyte detections than glucose. Thus, generally and as outlined above, any type of analyte may be detected which is detectable by using an optical test chemical, such as by using a photometric detection. As an example, lipids, such as one or more of TG, HDL and cholesterol; liver enzymes, such as one or more of GOT, GPT, gammaGT; HbA1c and/or further clinical parameters may be detected. The design of the test elements may be adapted to the prospected use, such as by providing a filling control, an impedance measurement for hematocrit and/or temperature control.

The test elements generally, as outlined above, may provide a wetting control. The wetting control generally may be provided by using conductivity measurements during filling of the capillary elements and/or by using other types of wetting detection mechanisms. Thereby, an easy control of a correct application of the sample of the body fluid and/or an information regarding a correct filling of a capillary element may be provided.

Specifically by using the above-mentioned cNAD test chemical, a high robustness and a low influence of redox-active substances may be provided. The enzyme glucose dehydrogenase and the stability of the co-factor cNAD is well suited for the present invention. However, additionally or alternatively, other types of test chemicals may be used alternatively or in addition.

The invention as disclosed above may also be applied to immunological tests and immunological test elements. Thus, as an example, reference may be made to EP0186799A1 and the device disclosed therein. This type of device may easily be equipped with an impedance measurement setup as disclosed above, such as by providing two or more impedance measurement electrodes and recording an impedance answer signal, thereby generating at least one impedance measurement value. The impedance measurement value may be used, in addition to the optical value generated by the immunological tests, to derive a corrected immunological test result. Additionally or alternatively, other types of immunological test elements may be used, preferably immunological test elements adapted for optical detection, which may be equipped with two or more impedance measurement electrodes, in order to be used according to the present invention. Therein, as outlined above, an optical measurement may be performed by using the immunological test element, according to method step a) as disclosed above. Further, the two or more impedance measurement electrodes may be used for performing at least one impedance measurement, according to method step b) as disclosed above, and at least one evaluation step, for evaluating the immunological tests, may be performed, by using both the optical measurement value generated in step a) and the impedance measurement value generated in step b), for determining the concentration of the at least one analyte of interest for the immunological test. Specifically, a correction for one or more interferents may be performed, as outlined above.

The impedance measurement may comprise a measurement of at least one admittance. Preferably, this measurement of at least one admittance may be performed by using aluminum, an aluminum alloy or an aluminum oxide as an electrode material for the impedance measurement electrodes.

For providing appropriate electrode structures for the impedance measurement electrodes, one or more layers of an electrically conductive material, such as one or more metal layers, may be applied to a substrate, such as a plastic substrate. The one or more metal layers preferably may have a thickness of 20 nm to 500 nm, more preferably a thickness of 50 nm to 150 nm. Thus, as an example, electrode patterns may be applied, directly or by using an inverse process, such as laser ablation or other patterning processes. An alternating current and/or voltage may be applied to the impedance measurement electrodes. The impedance measurement electrodes may have various or different geometries. The sample of the body fluid may wet the electrodes and, dependent e.g. on the concentration of an interferent such as dependent on hematocrit of the sample, different answer signals, such as different conductivity signals, may be measured.

Surprisingly, the measurements performed within the present invention have shown that impedance measurement electrodes, more specifically aluminum electrodes, do not necessarily have to be coated with a test chemistry. Thus, as an example, a passivating uniform oxide layer may be present on the surface of the electrode material and provides a high reproducibility of the measurement results during the impedance measurement, as well as a low noise.

Specifically aluminum electrodes may be used in a wide frequency range, such as 100 Hz to 400 kHz. Thus, besides the measurement of the hematocrit (HKT), a precise differentiation between the HKT and further interferences, such as temperature and/or salt content of the sample, may be performed. These other interferences may also have an influence on the conductivity and may be corrected in analogy to the hematocrit. The use of aluminum electrodes specifically is preferable in case the impedance measurement does not imply the use of any DC component, since, in case only alternating electrical signals are used, electrochemical dissolving, migration of aluminum ions or electrochemical oxidation is avoided.

Further, redox-active components such as pharmaceuticals, which may be present in the sample, have turned out not to show a significant impact on the impedance measurements, when aluminum electrodes are used.

Further, besides a metal electrode material, additionally or alternatively, other types of electrode materials may be used for the impedance measurement electrodes. Thus, besides aluminum, semiconducting materials and/or semiconducting coatings as well as metals and alloys, preferably having one or more passivation layers, may be used.

As outlined above, electrodes made of aluminum generally are rather cost-efficient, such as compared to typical gold electrodes. Aluminum may be applied to the substrate by using standard techniques, such as physical vapor deposition and/or chemical vapor deposition. As an example, the electrodes may be sputtered onto the substrate, such as onto a flexible substrate. These technologies are widely used in packaging technologies, such as for food. For patterning aluminum, simple techniques may be used such as laser ablation.

Aluminum is known to be widely harmless in view of environmental requirements, as opposed to metals like nickel or copper. Still, aluminum may be used as an electrode material for AC measurement methods, in analogy to electrodes made of gold. Further, the adhesion of the aluminum electrodes to typical substrate materials, such as plastic materials and, more preferably, plastic foils, is known to be excellent, and aluminum may easily be contacted.

Further, as outlined above, aluminum electrodes generally are not affected by the presence of reversible redox components. Thus, passivating $Al_2O_3$ surface layers may impede a heterogeneous electron transfer. Thereby, an interference by redox-active substances in the sample, such as pharmaceuticals, may be reduced or even avoided. The same holds true for other types of metals which form an oxide surface layer, such as tantalum. Some advantages and disadvantages of other electrode materials, which may be used additionally or alternatively, will be explained in further detail below.

The passivating oxide layer further renders aluminum highly stable, such as in a pH range of 4 to 9, specifically against corrosion. Therefore, specifically for measuring hematocrit, the electrodes made of aluminum may be uncoated and not chemically treated. Contrarily, gold surfaces have to be protected from oxidation. Consequently, as outlined above, aluminum electrodes not necessarily have to be cleaned before use, such as by using plasma cleaning, as opposed to e.g. gold. Thus, the substrate material coated by aluminum, such as an aluminum-coated foil material, generally exhibits a good long-term stability and may easily be stored.

Summarizing the findings of the present invention, the following embodiments are preferred:

Embodiment 1

A method for detecting at least one analyte in a body fluid, the method comprising the following steps:
a) performing an optical measurement, wherein at least one test chemical is contacted with the body fluid, wherein the test chemical is an optical test chemical and is adapted to perform at least one detection reaction in the presence of the analyte, wherein at least one optically detectable property of at least one of the body fluid and the test chemical is changed due to the detection reaction, wherein at least one optical measurement value is generated;
b) performing at least one impedance measurement, wherein at least two impedance measurement electrodes are used, wherein at least one alternating electrical signal is applied to the body fluid via the impedance measurement electrodes and wherein at least one answer signal is recorded, wherein at least one impedance measurement value is generated;
c) performing at least one evaluation step, wherein, in the evaluation step, at least one evaluation algorithm is used, wherein the optical measurement value and the impedance measurement value are used for determining a concentration of the analyte in the body fluid.

Embodiment 2

The method according to the preceding embodiment, wherein step c) comprises at least one failsafe step, wherein, in the failsafe step, one or both of the optical measurement value or the impedance measurement value are used.

Embodiment 3

The method according to the preceding embodiment, wherein the failsafe step comprises comparing at least one of the optical measurement value or the impedance measurement value or one or more secondary measurement values derived thereof with at least one threshold value, specifically with at least one out-of-range threshold value.

Embodiment 4

The method according to any one of the two preceding embodiments, wherein the failsafe step comprises comparing at least one parameter with at least one threshold value, specifically at least one parameter selected from the group consisting of: an interferent concentration, specifically a hematocrit; an environmental parameter, specifically a temperature of a surrounding environment; an experimental parameter, specifically a degree of filling of a capillary element and/or a degree of wetting of a test chemical; a sample parameter, specifically a sample temperature.

Embodiment 5

The method according to any one of the three preceding embodiments, wherein the method is stopped in case, in the failsafe step, a failure is detected.

Embodiment 6

The method according to the preceding embodiment, wherein the body fluid is selected from the group consisting of: blood, preferably whole blood; interstitial fluid; urine; saliva.

Embodiment 7

The method according to one of the preceding embodiments, wherein the analyte is selected from the group consisting of: glucose; lactate; triglycerides; ketone; ethanol; total cholesterol; HDL cholesterol; LDL cholesterol; urea; uric acid; creatinine; ammonia; alkaline phosphatase (ALP); creatine kinase (CK); amylaea; pancraetic amylase; (Gamma)-Glutamyltransferase (GGT); Glutamic-oxaloacetic transaminase (GOT); Glutamic-pyruvic transaminase (GPT); bilirubin; hemoglobin; potassium; a substances or a combination of substances involved in the intrinsic and/or extrinsic coagulation pathway.

Embodiment 8

The method according to one of the preceding embodiments, wherein the test chemical comprises at least one enzyme.

Embodiment 9

The method according to one of the preceding embodiments, wherein, in step c), the concentration of the analyte in the body fluid is a corrected concentration which is corrected for at least one interferent concentration in the body fluid.

Embodiment 10

The method according to the preceding embodiment, wherein the interferent is selected from the group consisting of: a drug; a disinfectant; a redox reactive substance; ascorbic acid; a peroxide; a glutathione; a particulate component in the body fluid, preferably at least one cellular component in the body fluid and, more preferably, a hematocrit.

Embodiment 11

The method according to one of the preceding embodiments, wherein step c) comprises the following substeps:
c.1) determining an estimated value of the concentration of the analyte in the body fluid by using the optical measurement value and a first evaluation algorithm;
c.2) determining a corrected value of the concentration of the analyte in the body fluid by using the estimated value and correcting the estimated value by using at least one correction algorithm, wherein the correction algorithm uses the impedance measurement value.

Embodiment 12

The method according to one of the preceding embodiments, wherein a single test element is used for both method step a) and method step b).

Embodiment 13

The method according to the preceding embodiment, wherein the test element comprises a substrate and the at least two impedance measurement electrodes applied to the substrate, wherein the test element further comprises at least one test field connected to the substrate, wherein the test field comprises the test chemical.

Embodiment 14

The method according to the preceding embodiment, wherein the test field is spatially separated from the impedance measurement electrodes.

Embodiment 15

The method according to one of the three preceding embodiments, wherein the test element comprises at least one application location, wherein a sample of the body fluid is applied to the application location.

Embodiment 16

The method according to the preceding embodiment, wherein the test element comprises at least one capillary element, wherein the capillary element is adapted for conducting the sample of the body fluid from the application location to at least one of the test chemical and the impedance measurement electrodes.

Embodiment 17

The method according to one of the preceding embodiments, wherein at least one impedance measurement electrode of the at least two impedance measurement electrodes comprises a metal selected from the group consisting: of molybdenum, tungsten, tantalum, niobium, zirconium, titanium, ruthenium, rhodium, iridium, palladium, platinum, silver, gold; and preferably aluminum.

Embodiment 18

The method according to one of the preceding embodiments, wherein the impedance measurement electrodes are bare metal electrodes.

Embodiment 19

The method according to one of the preceding embodiments, wherein the impedance measurement electrodes are in direct contact with the body fluid during the impedance measurement.

Embodiment 20

The method according to one of the preceding embodiments, wherein the impedance measurement implies at least one of: an application of a sinusoidal voltage to the impedance measurement electrodes and a measurement of an electrical current through the impedance measurement electrodes as an answer signal, preferably for a plurality of frequencies; an application of a sinusoidal electrical current to the impedance measurement electrodes and a measurement of a voltage required to obtain the electrical current as an answer signal, preferably for a plurality of frequencies.

Embodiment 21

The method according to one of the preceding embodiments, wherein the impedance measurement implies a measurement of at least one of the following parameters of the sample: a conductivity, preferably a complex electrical conductivity; an admittance; a phase shift; a permittivity; an impedance, preferably a complex impedance; a real part, specifically a real part related to admittance and/or impedance; an imaginary part, specifically an imaginary part related to admittance and/or impedance.

Embodiment 22

The method according to one of the preceding embodiments, wherein a wetting control of at least one element selected from the group consisting of the impedance measurement electrode and the test chemical is performed by using the impedance measurement electrodes.

Embodiment 23

The method according to the preceding embodiment, wherein a filling of a capillary element is monitored by using the at least one impedance measurement value.

Embodiment 24

A test element for detecting at least one analyte a body fluid, the test element comprising:
a) at least one test chemical which may be contacted with the body fluid, the test chemical being an optical test chemical and being adapted to perform at least one detection reaction in the presence of the analyte, wherein at least one optically detectable parameter of at least one of the body fluid and the test chemical is changed due to the detection reaction;
b) at least two impedance measurement electrodes adapted for applying an alternating electrical signal to the body fluid and adapted to record at least one answer signal.

Embodiment 25

The test element according to the preceding embodiment, wherein the test element is adapted for use in the method according to one of the preceding embodiments referring to a method.

Embodiment 26

The test element according to one of the two preceding embodiments, wherein at least one impedance measurement electrode of the at least two impedance measurement electrodes comprises a metal selected from the group consisting of: molybdenum, tungsten, tantalum, niobium, zirconium, titanium, ruthenium, rhodium, iridium, palladium, platinum, silver, gold; and preferably aluminum.

Embodiment 27

The test element according to one of the preceding embodiments referring to a test element, wherein the impedance measurement electrodes are bare metal electrodes.

Embodiment 28

The test element according to one of the preceding embodiments referring to a test element, wherein the impedance measurement electrodes are in direct contact with the body fluid during the impedance measurement.

Embodiment 29

The test element according to one of the preceding embodiments referring to a test element, wherein the test element is selected from the group consisting of a test strip, a test tape, a test disc.

Embodiment 30

The test element according to one of the preceding embodiments referring to a test element, wherein the test element comprises at least one substrate and the at least two impedance measurement electrodes applied to the substrate, wherein the test element further comprises at least one test field connected to the substrate, wherein the test field comprises the test chemical.

Embodiment 31

The test element according to the preceding embodiment, wherein the test field is spatially separated from the impedance measurement electrodes.

Embodiment 32

The test element according to one of the preceding embodiments referring to a test element, wherein the test element comprises at least one application location, wherein a sample of the body fluid is applicable to the application location.

Embodiment 33

The test element according to the preceding embodiment, wherein the test element further comprises at least one capillary element, wherein the capillary element is adapted for conducting the sample of the body fluid from the application location to at least one of the test chemical and the impedance measurement electrodes.

Embodiment 34

The test element according to one of the preceding embodiments referring to a test element, wherein the at least one optically detectable property is selected from the group consisting of: a color of the test chemical; a reflection property of the test chemical, preferably a remission of a test field comprising the test chemical; a fluorescence of the test chemical.

Embodiment 35

A measurement system for detecting at least one analyte in a body fluid, the measurement system comprising:
i) at least one test element according to one of the preceding embodiments referring to a test element;
ii) at least one measurement device adapted for using the test element, wherein the measurement device is adapted to perform the method according to one of the preceding embodiments referring to a method.

Embodiment 36

The measurement system according to the preceding embodiment, wherein the measurement device comprises at least one test element receptacle adapted for receiving the test element.

Embodiment 37

The measurement system according to one of the preceding embodiments referring to a measurement system, wherein the measurement device comprises at least one optical detector, wherein the optical detector is adapted to measure the at least one optically detectable property and to generate the at least one optical measurement value.

Embodiment 38

The measurement system according to the preceding embodiment, wherein the optical detector comprises at least one light source for illuminating at least part of the test chemical and wherein the optical detector further comprises at least one light-sensitive element for detecting light propagating from the test chemical to the optical detector.

Embodiment 39

The measurement system according to one of the preceding embodiments referring to a measurement system, wherein the measurement device further comprises at least one impedance measurement device, wherein the impedance measurement device is connectable to the impedance measurement electrodes and wherein the impedance measurement device is adapted to perform the impedance measurement.

Embodiment 40

The measurement system according to the preceding embodiment, wherein the impedance measurement device comprises at least one alternating voltage source, wherein the alternating voltage source is adapted to apply at least one alternating voltage signal to the body fluid via the impedance measurement electrodes, and at least one current measurement device, wherein the current measurement device is adapted to measure at least one electrical current through at least one of the impedance measurement electrodes.

Embodiment 41

The measurement system according to the preceding embodiment, wherein the alternating voltage source is adapted to generate alternating voltage signals at a plurality of frequencies.

Embodiment 42

The measurement system according to one of the two preceding embodiments, wherein the current measurement device is adapted to measure the electrical current in a phase-sensitive way.

Embodiment 43

The measurement system according to one of the four preceding embodiments, wherein the impedance measurement device comprises at least one alternating current source, wherein the alternating current source is adapted to induce at least one alternating electrical current through the body fluid via the impedance measurement electrodes, and at least one voltage measurement device, wherein the voltage measurement device is adapted to measure at least one voltage required to induce the alternating electrical current.

Embodiment 44

The measurement system according to the preceding embodiment, wherein the alternating current source is adapted to induce alternating electrical currents at a plurality of frequencies.

Embodiment 45

The measurement system according to one of the two preceding embodiments, wherein the voltage measurement device is adapted to measure the voltage in a phase-sensitive way.

Embodiment 46

The measurement system according to one of the preceding embodiments referring to a measurement system, wherein the measurement device further comprises at least one evaluation unit, wherein the evaluation unit is adapted to determine the concentration of the analyte in the body fluid by performing at least one evaluation algorithm, by using the at least one optical measurement value and the at least one impedance measurement value.

Embodiment 47

The measurement system according to the preceding embodiment, wherein the evaluation unit comprises at least one data processing device.

Embodiment 48

The measurement system according to one of the two preceding embodiments, wherein the evaluation unit is further adapted to detect a wetting of at least one of the test chemical, the impedance measurement electrode and a capillary element by using the at least one impedance measurement value.

Embodiment 49

The measurement system according to the preceding embodiment, wherein the evaluation device is adapted to monitor a filling of at least one capillary element.

Embodiment 50

A use of aluminum as an electrode material for electrodes for performing impedance measurements in a body fluid.

Embodiment 51

The use according to the preceding embodiment, wherein, by the impedance measurement, a concentration of at least one interferent in the body fluid is determined.

Embodiment 52

The use according to one of the two preceding embodiments, wherein the electrodes contain aluminum in one of a pure form, as an alloy and as an oxide.

In FIG. 1, a highly simplified and schematic cross-sectional view of a measurement system 110 for detecting at least one analyte in a body fluid 112 is depicted. The measurement system 110 comprises a test element 114 which, in this preferred embodiment, is embodied as a test strip. The measurement system 110 further comprises at least one measurement device 116. The measurement device 116 comprises a test element receptacle 117 for receiving the test element 114.

The test element 114, in this embodiment, may comprise at least one test field 118 having at least one test chemical 120 therein. The test field 118 is applied to a substrate 122 which, in this specific embodiment, comprises a plurality of layers spaced apart by one or more spacers 124. Thereby, a capillary element 126 is formed within the test element 114, which allows for transporting a sample of the body fluid 112 from an application location to the test field 118. The test field 118 may be contacted by the body fluid 112 via the capillary element 126. Further, inside the capillary element 126, at least two impedance measurement electrodes 130 are provided, which may be contacted via contact leads (not shown in FIG. 1) and contact pads 132.

The test chemical 120 is adapted to change at least one optically detectable property due to a detection reaction. This at least one optically detectable property may be observed and/or measured or monitored via at least one detection window 134 by at least one optical detector 136.

The optical detector 136 may comprise at least one light source 138 for illuminating the test field 118, such as at least one light-emitting diode and/or any other type of light source, and may comprise at least one light-sensitive element 140 for detecting light propagating from the test field 118 to the optical detector 136, such as reflected light and/or light emitted by the test field 118.

The measurement device 116 further comprises at least one impedance measurement device 142 which may interact with the at least two impedance measurement electrodes 130. Thus, the measurement device 116 may comprise one or more contacting elements 144, such as one or more contact pins and/or contact springs, which may electrically contact the contact pads 132. Further, the impedance measurement device 142 may comprise an alternating electrical source 146, such as an alternating current source and/or an alternating voltage source. Further, the impedance measurement device 142 may comprise one or more measurement devices 148, such as one or more of a current measurement device and/or a voltage measurement device. The alternating electrical source 146 and the measurement device 148 are depicted symbolically in FIG. 1.

The measurement device 116 as depicted in FIG. 1 may further comprise at least one evaluation unit 150. The evaluation unit may be adapted to use at least one optical measurement value as provided by the optical detector 136 and/or as derived from at least one signal provided by the optical detector 136, and at least one impedance measurement value, as provided by the impedance measurement device 142 and/or as derived from at least one signal provided by the impedance measurement device 142, and to perform at least one evaluation algorithm by using the optical measurement value and the impedance measurement value. Thus, as will be outlined in further detail below, the evaluation unit 150 preferably is adapted to provide at least one corrected value of the analyte concentration in the body fluid 112, the corrected value being corrected for the concentration of at least one interferent in the body fluid 112, such as being corrected for a hematocrit.

The measurement device 116 may further comprise one or more user interfaces, such as one or more of a display 152 and/or one or more control elements 154. Further, one or more wirebound and/or one or more wireless electronic interfaces 156 may be provided. Further, the measurement device 116 may comprise one or more power supplies. Thus, one or more integrated power supplies, such as one or more batteries and/or accumulators, may be provided. Additionally or alternatively, an external power supply may be provided, such as via a plug and/or a cable. The power supply is not depicted in FIG. 1.

It shall be noted that the measurement system 110 as depicted in FIG. 1, in which the measurement device 116 preferably is a hand-held device comprising all components of the measurement device 116 within a casing 158, is only one exemplary embodiment of measurement systems 110 according to the present invention. Thus, besides embodiments in which the measurement device 116 is formed by a hand-held device, stationary measurement devices 116 may be used. Further, instead of using measurement devices 116 having one single component only, measurement devices 116 being composed of a plurality of interacting components may be used.

Figure 2:
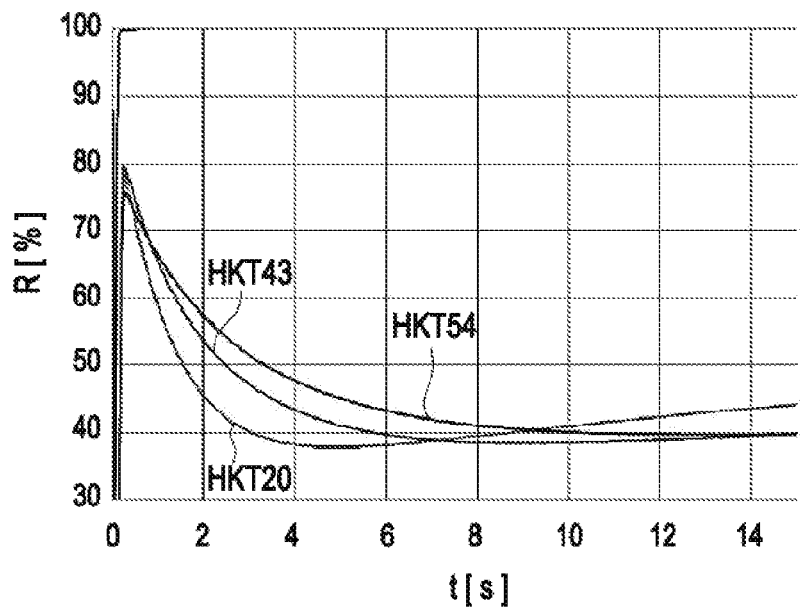
FIG. 2 shows optical measurement curves of typical optical glucose measurements for different hematocrits.

In FIG. 2, typical optical measurement curves, which are composed of a sequence of remission values R, given in percent, are depicted as a function of time t, given in seconds. The measurement curves are provided for three different hematocrit values, HKT=20 vol.-%, HKT=43 vol.-% and HKT=54 vol.-%. The HKT was measured independently by using an electrical conductivity. The data shown are the results of remission measurements (wavelength=360 nm) for a standard glucose amount of 1 mg and using carba-NAD (cNAD) as an optical detection reagent.

The measurements in FIG. 2 clearly show that the measurement curves significantly are influenced by the HKT. Thus, the lower the hematocrit of the sample, the faster the enzymatic detection reaction will proceed, as indicated by a higher negative initial slope of the curves.

Figure 3:
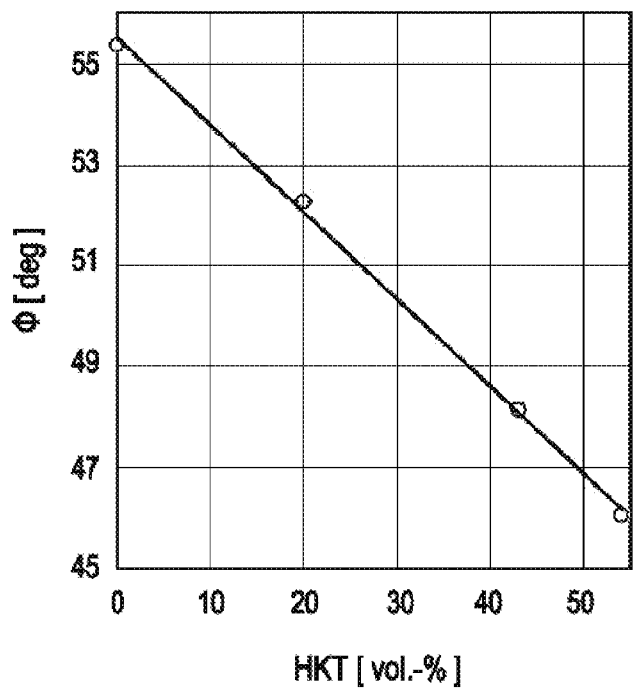
FIG. 3 shows a dependency of the phase Φ on the hematocrit HKT.

In FIG. 3, impedance measurements are shown for various blood samples having different hematocrits. Therein, the phase angle $\Phi$ is given in percent, as a function of the hematocrit HKT, given in vol.-%. As can be seen, the impedance measurement strongly correlates to the HKT. Thus, by using an appropriate evaluation algorithm, the optical signal may be corrected by using the impedance measurement signal. Thereby, a more precise measurement result for optical test elements may be provided.

Thus, as an example, an end value of the optical measurement curves in FIG. 2 may be determined and used as an optical measurement value. For this purpose, the slope of the optical measurement curves in FIG. 2 may be compared to one or more thresholds. For exemplary embodiments of this method, reference may be made to the prior art documents cited above. Thus, as an example, the end value of the measurement curve may be determined once the slope of the optical measurement curve (or the absolute value of the slope) falls below 2%. The remission value of the measurement curve at this point may be used as the optical measurement value and/or the optical measurement value may be derived thereof. Thus, by using the end value and a known correlation of the end value with the glucose concentration, a glucose concentration may be derived, which is an estimated glucose concentration. By using the hematocrit derived from the measurement in FIG. 3, an additional correction algorithm may be applied to the estimated value, such as by applying an appropriate known correction factor to the estimated glucose concentration. Thus, by using one or more impedance measurement values, such as the phase and/or the admittance, and further by using at least one known correlation between a correction factor and the impedance measurement value, an appropriate correction factor may be chosen. Thus, as an example, an appropriate correction factor for the actual hematocrit value of the sample of the body fluid may be chosen and may be applied to the estimated glucose concentration. Thereby, a corrected glucose concentration may be derived.

In analogy to the hematocrit, the influence of the temperature may be determined by the impedance measurement and may be used for a temperature correction of the photometric detection. Thus, as opposed to the use of temperature sensors within the measurement device, the actual temperature at the location of measurement may be determined, in conjunction with the sample of the body fluid. Thereby, deviations between the actual temperature of the measurement device and the sample of the body fluid at the location of measurement may be taken into account.

Figure 4:
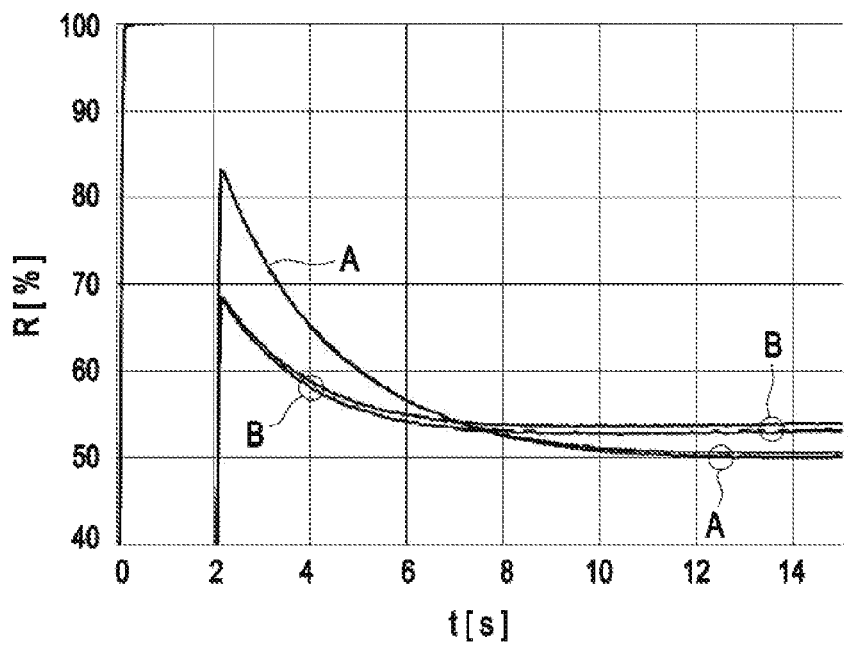
FIG. 4 shows an impact of the filling of a capillary element onto typical optical measurement curves.

Further, as outlined above, in addition to correcting the optical measurement for the presence and/or concentration of one or more interferents such as correcting for the hematocrit, and/or for the actual temperature, a wetting control of the test element 114 may be performed, such as a control of a filling of the capillary element 126. This wetting control may also be performed via conductivity measurements. Consequently, via an appropriate geometry of the impedance measurement electrodes 130 and/or additional wetting or filling electrodes which may optionally be provided in the test element 114, a wetting of the test chemical 120 and/or the test field 118 may be detected. Thus, typically, for a precise optical measurement, a complete wetting of the test field 118 is desirable, specifically a fast and efficient wetting. In FIG. 4, remission curves, similar to the remission curves provided in FIG. 2, are given for different wetting states and/or different fillings of the capillary element 126 by the sample of the body fluid 112. The curves denoted by "A" refer to remission curves detected by using complete and appropriate fillings of the capillary element 126, wherein curves B were detected with incomplete filling. For performing these measurements, the same sample was applied to a test element 114 having a capillary with a good wetting behavior (curves A) and to test elements 114 having a capillary with an incomplete wetting behavior, i.e. with insufficient wetting properties. In both test elements, the measurement was started after complete filling of the capillaries.

In curves A and B, it is evident that, in test elements having an incomplete filling, the enzymatic reaction has started before the start of the measurement. This example clearly shows that a control of a wetting of the test field 118 may be essential and that a filling time of the capillaries may be monitored.

Figure 5:
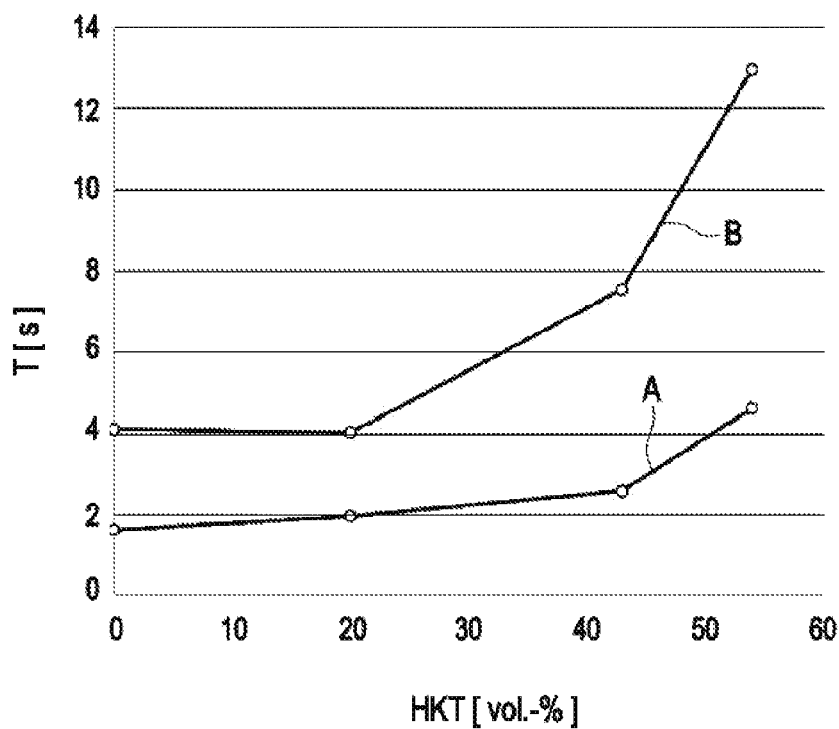
FIG. 5 shows an impact of the hematocrit HKT onto the filling time of a capillary element.

In FIG. 5, a filling time T (given in seconds, s) is depicted as a function of the hematocrit HKT, given in vol.-%, for the two different types of capillaries discussed above. Thus, again, curve A denotes a capillary having good wetting properties, whereas curve B refers to a capillary having insufficient wetting properties. By using an appropriate filling control via the impedance measurement, the detection reaction may be synchronized with the optical measurement.

Figure 6A:
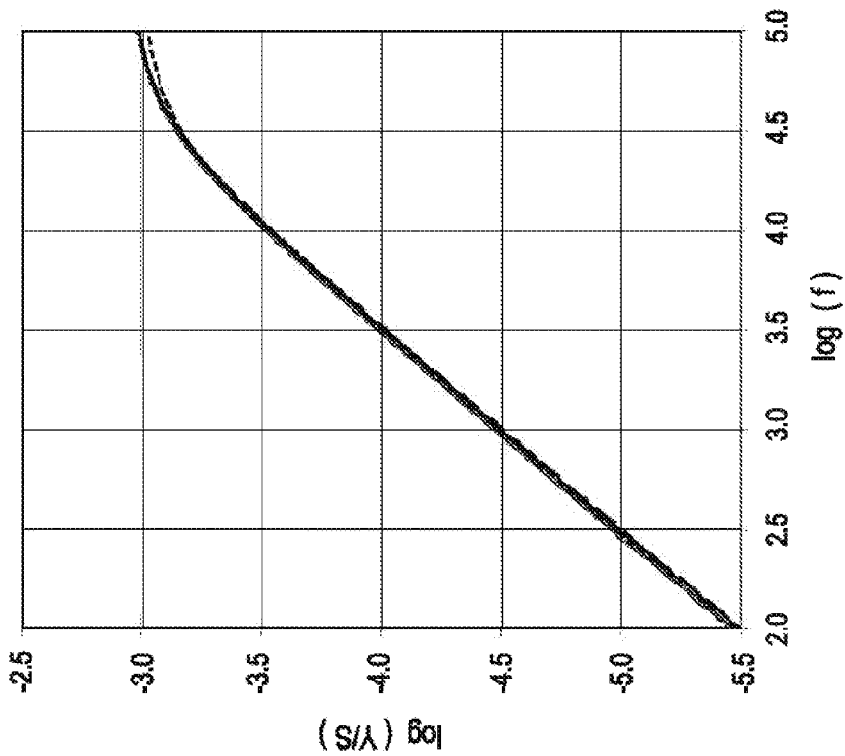
FIG. 6A shows typical admittance spectra for gold impedance measurement electrodes for various glucose contents.
Figure 6B:
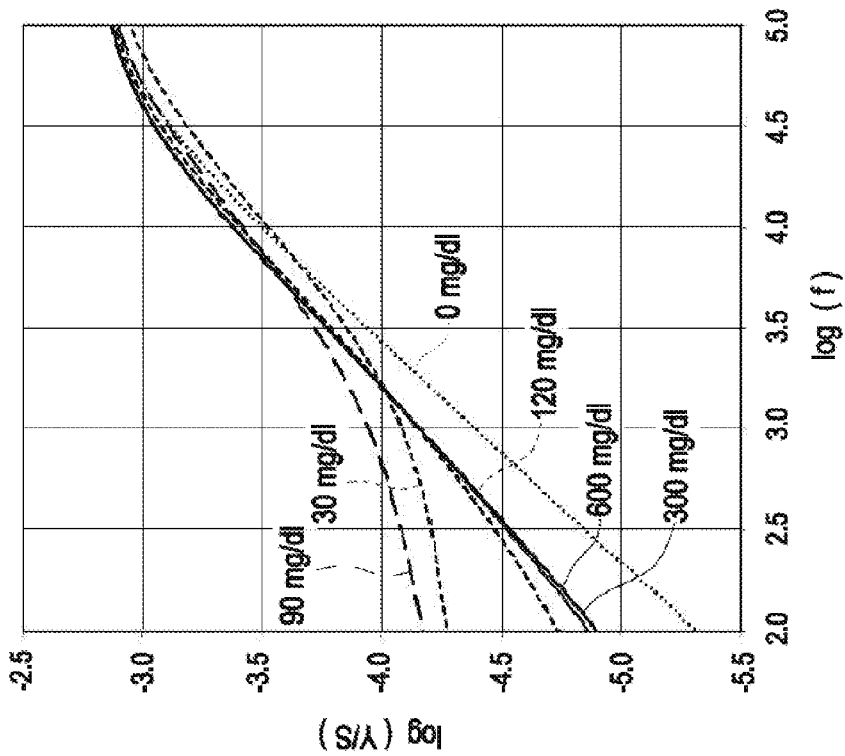
FIG. 6B shows typical admittance spectra for aluminum impedance measurement electrodes for various glucose contents.

Further preferred embodiments refer to the preferred use of aluminum or other materials forming a surface oxide layer as an electrode material for the impedance measurement electrodes 130. Thus, in FIGS. 6A and 6B, admittance spectra are depicted for gold impedance measurement electrodes 130 (FIG. 6A) and aluminum impedance measurement electrodes 130 (FIG. 6B). Therein, the admittance, denoted by Y, given in Siemens S (1 S=1 A/V=1/Ω), is depicted on the vertical axis in logarithmic units, and the frequency F of the alternating electric signal is provided on the horizontal axis in logarithmic units, too.

The admittance spectra are given for various concentrations of glucose in whole blood. Thus, as can be seen in FIG. 6A, admittance spectra for 0, 30, 90, 120, 300 and 600 mg/dl glucose in whole blood are given. In addition to these respective glucose concentrations, a reagent comprising glucosedehydrogenase, carba-NAD (cNAD) and a *phenazinium* mediator (as an exemplary reversible redox mediator substance which can interfere with the glucose determination) is added to the samples. The same concentrations are used in FIG. 6B, even though the curves may not be resolved in this case.

The measurements in FIG. 6A were performed by using gold electrodes of a test strip. The measurements show a significant dependency of the admittance on the concentration ratio of an oxidized and a reduced form of a reversible redox mediator, as may be used in the detection of glucose. This redox mediator may be a pharmaceutical which is given to a patient before glucose measurement and which is electrochemically active, i.e. which may be oxidized or reduced at the working electrode.

The higher the glucose concentration, the higher the mediator may be reduced. Consequently, both the reduced form and the oxidized form of the mediator are present. As can be seen in FIG. 6A, the influence of the glucose concentration on the admittance spectra at the gold impedance measurement electrodes is rather high. Contrarily, in the spectra in FIG. 6B, using aluminum impedance measurement electrodes, the admittance spectra are not affected by the actual glucose concentration and are more or less identical over the whole range of glucose concentrations.

Figure 7:
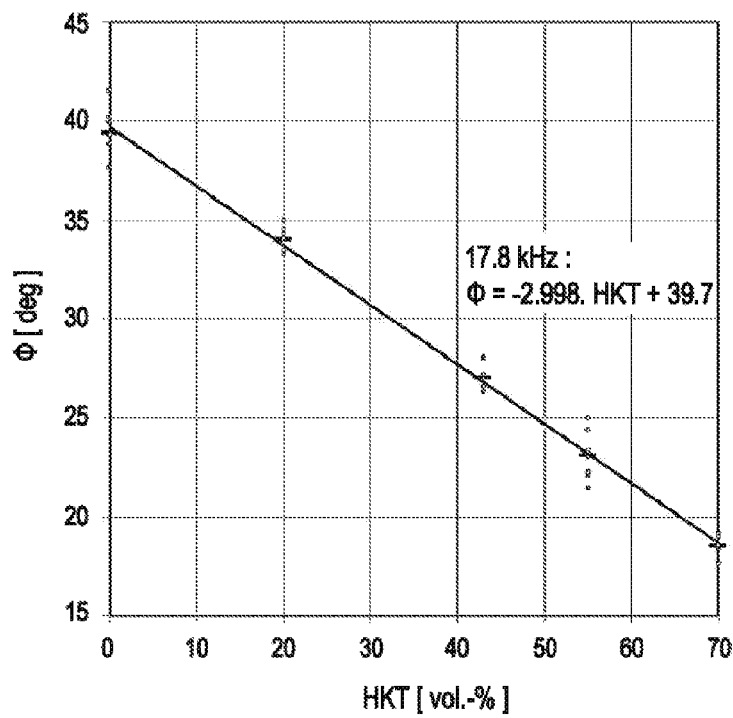
FIG. 7, in analogy to FIG. 3, shows an impact of the hematocrit HKT on the phase (I) for impedance measurements using aluminum as an electrode material of the impedance measurement electrodes.

In order to further test the aluminum electrodes, in FIG. 7, in analogy to the measurement in FIG. 3, aluminum impedance measurement electrodes were used for generating phase spectra in the range of 1 kHz to 100 kHz. As a sample material, whole blood was used, in samples having different hematocrit values.

In FIG. 7, various measurement points of the phase, determined by admittance spectroscopy, for the various frequencies, are depicted as a function of the HKT of the respective sample. Immediately, a linear dependency may be recognized.

As an example for further evaluation, a frequency of f=17.8 kHz was selected. Again, uncoated aluminum impedance measurement electrodes were used, which allowed for a measurement of the HKT at a very high precision.

For determining the hematocrit and/or other interferents, various impedance measurement values may be used. Thus, as an example, one or more of the following impedance measurement values may be used: The admittance, a phase shift Φ, a real part of the impedance (Ri), an imaginary part of the impedance (Im). Therein, obviously, the admittance (Y) and the phase shift (Φ) may be calculated mathematically from the real part and the imaginary part:

$$|Y|=\sqrt{[Re^2(Y)+Im^2(Y)]} \quad (1)$$

$$\Phi=\arctan\,[Im(Y)/Re(Y)] \quad (2)$$

It shall be noted, however, that the proposed embodiments may be replaced and/or may be completed by one or more additional parameters or measurement values which may be replaced and/or may be completed by one or more additional parameters or measurement values which may be drawn from impedance measurements.

Figure 8:
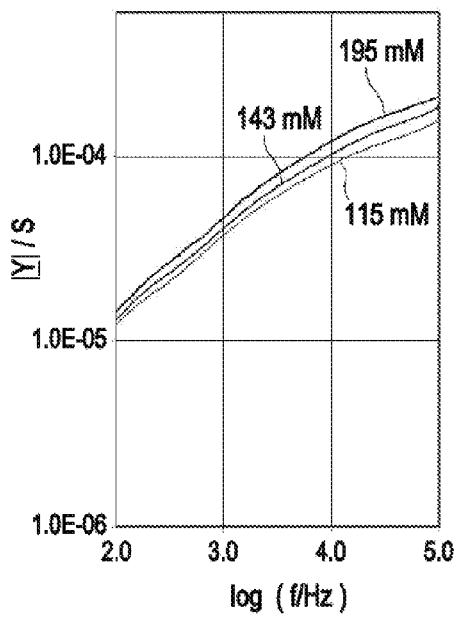
FIG. 8A shows admittance spectra for gold impedance measurement electrodes for various concentrations of NaCl.
FIG. 8B shows admittance spectra for aluminum impedance measurement electrodes for various concentrations of NaCl.
Figure 8:
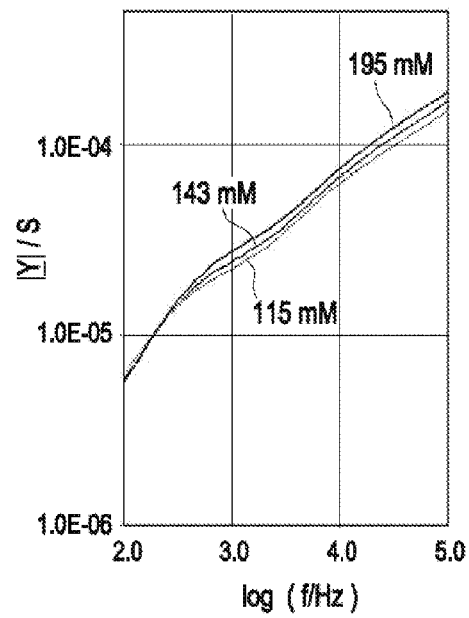

Further, measurements were performed in analogy to the measurements of samples having different hematocrit values, with the concentration of other constituents of the sample varied. Thus, in FIGS. 8A and 8B, admittance spectra, in a plot corresponding to FIGS. 6A and 6B, are given as a function of the frequency f of the alternating electrical signal. In this case, samples having a different concentration of salt (NaCl) were used. Again, FIG. 8A shows measurements for gold impedance measurement electrodes, whereas FIG. 8B shows measurements using aluminum impedance measurement electrodes. The measurements were taken as a temperature of 22° C., with a hematocrit value of 43 vol.-%, for NaCl concentrations of 115, 143 and 195 mmol.

As can be seen, both electrode materials, i.e. Au and Al, behave in a similar way in this case of inert, non-redox active constituent concentration variations.

Figure 9:
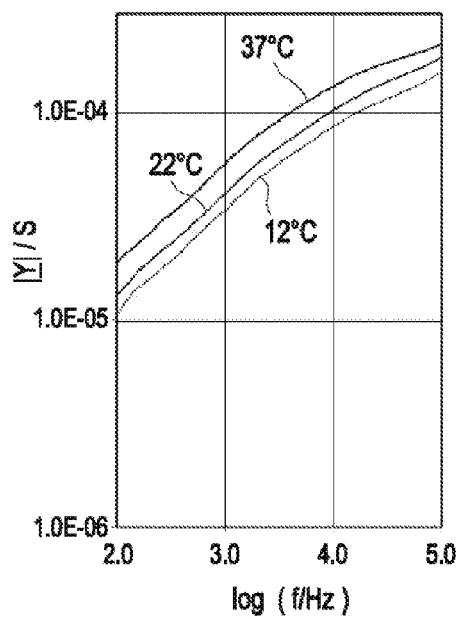
FIG. 9A shows admittance spectra for gold impedance measurement electrodes for various temperatures.
FIG. 9B shows admittance spectra for aluminum impedance measurement electrodes (FIG. 9B) for various temperatures.
Figure 9:
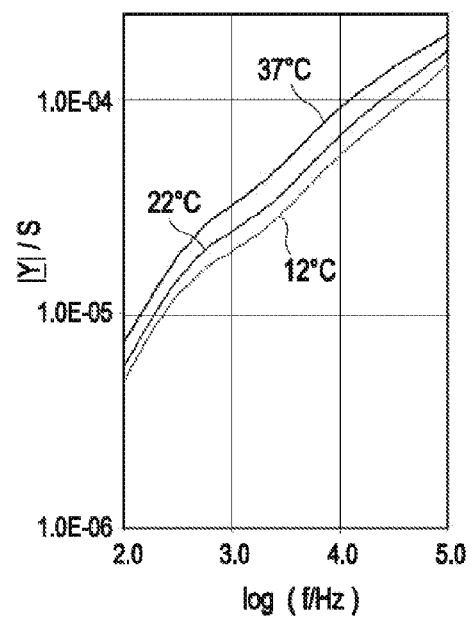

Further, measurements taking into account different temperatures were performed. These measurements are shown in FIGS. 9A and 9B, in a fashion similar to FIGS. 8A and 8B. Again, FIG. 9A shows impedance measurements using gold as an impedance measurement electrode material, whereas FIG. 9B shows impedance measurements using aluminum as the impedance measurement electrode material. The frequency spectra were taken at different environmental temperatures, at 12° C., 22° C. and 37° C. As can be seen, both electrode materials may be used. Further, as can be seen, the admittance spectra may be used for deriving information regarding the temperature and, thus, for providing a temperature correction. As opposed to typical temperature measurements, by using impedance measurement values, temperatures immediately at the location of the optical detection and/or temperatures of the sample itself may be detected, which may deviate from the ambient temperatures measured by typical temperature sensors.

Further, as discussed above, a wetting control, specifically a filling control of the at least one capillary element, may be provided by using the admittance measurement electrodes 130 and/or additional filling control or wetting electrodes. For this purpose, again, aluminum electrodes are preferred.

Figure 10:
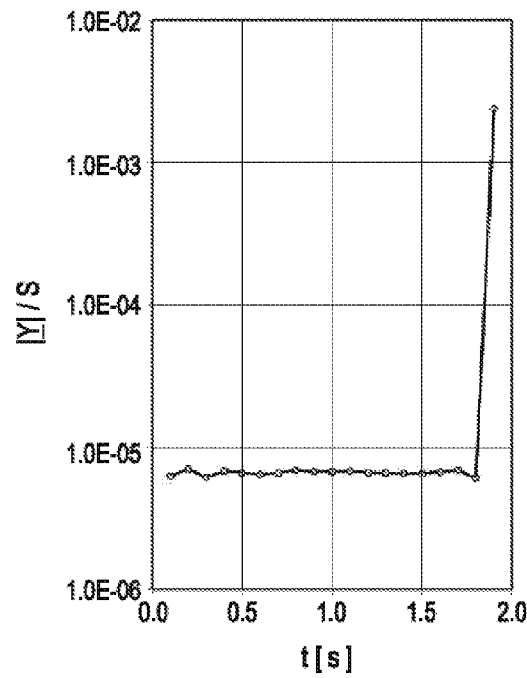
FIG. 10 shows a time development of an admittance during filling of a capillary element and the detection of a filling time.
Figure 11:
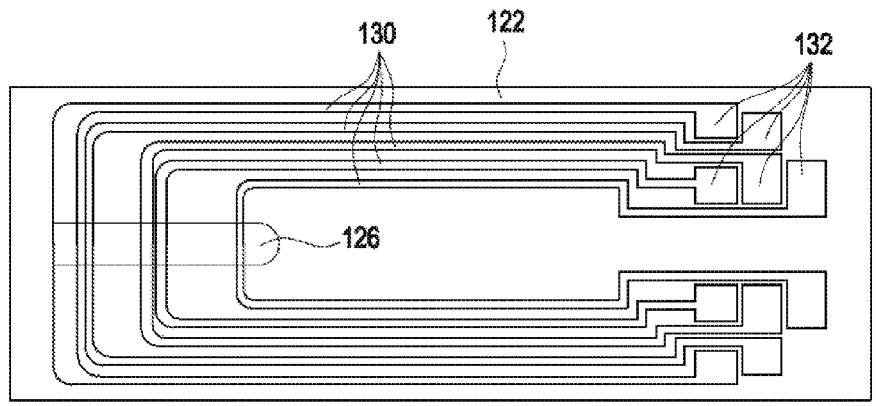
FIG. 11 shows an electrode setup of impedance measurement electrodes which may be used for wetting detection, specifically for filling detection of a capillary element.

In FIG. 10, admittance values as a function of time t during filling of a capillary element are depicted. For this purpose, a setup as depicted in FIG. 11 was used, having a substrate 122 with a capillary element 126 and a plurality of impedance measurement electrodes 130 disposed thereon. The impedance measurement electrodes 130 may be contacted via contact pads 132.

As can be seen in the time development of the admittance in FIG. 10, the conductivity and the admittance are significantly increased when the aluminum electrodes are wetted by the sample. This principle may be used for detecting and controlling a wetting and/or a filling of the capillary element 126. In case a plurality of electrodes, i.e. the impedance measurement electrodes 130 and/or additional electrodes, are provided in the test element 114, this principle of measurement may detect a filling of the capillary element 126 and/or any other type of wetting. The wetting control may be used as a failsafe mechanism for controlling a filling of the capillary element 126.

Figure 12:
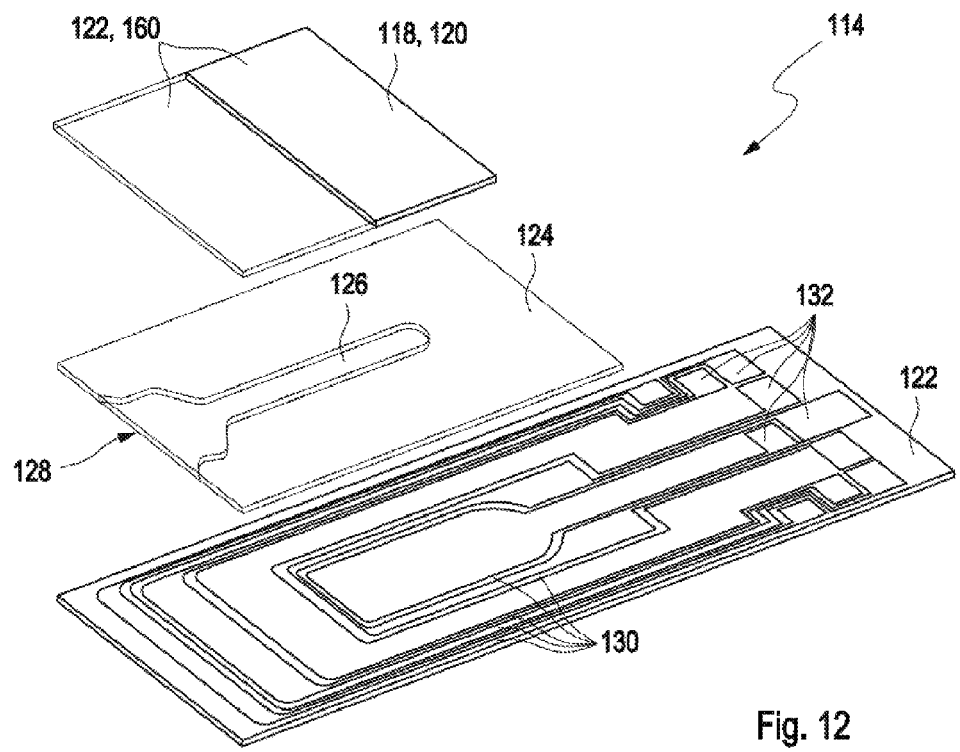
FIG. 12 shows an explosion view of an embodiment of a test element 114 according to the present invention.

In FIG. 12, an exemplary embodiment of a test element 114 is depicted in an explosion view. The test element 114 comprises a substrate 122, such as a flexible plastic substrate. As an example, a polycarbonate and/or polyester foil may be used. On the substrate 122, a plurality of impedance measurement electrodes 130 is depicted, which, fully or partially, may also be used for the purpose of wetting control, specifically of filling control, for a capillary element 126 within the test element 114.

The test element 114 further comprises a test field 118 which, in turn, comprises at least one test chemical 120. Further, one or more cover foils 160 may be comprised, which, fully or partially, may be transparent, specifically in the region of the test field 118. The cover foils 160 may also be considered as a part of the at least one substrate 122.

Further, the test element 114 comprises one or more spacers 124 inserted in between the bottom substrate 122 carrying the impedance measurement electrodes and the top cover foils 160. Thus, the bottom substrate 122, in combination with the spacer 124 and the cover foils 160, form the capillary element 126. At a front side of the capillary element 126, one or more application positions 128 may be provided, at which the sample of the body fluid 112 (not depicted) may be applied to the capillary element 126, in order to initiate a filling of the capillary element 126. By using contact pads 132 of the impedance measurement electrodes 130, both a wetting control of the capillary element 126, specifically a filling control, and/or the above-mentioned impedance measurement may be performed. The optical measurement may be performed through the transparent cover foil 160 and/or from the backside of the test field 118. For further details, reference may be made to the above-mentioned description of FIG. 1.

It shall be noted that FIG. 12 simply discloses one potential embodiment of the test element 114. Other embodiments are feasible. Thus, in the embodiment of FIG. 12, two counterpart substrates 122 are provided, wherein the lower substrate 122 (bottom substrate) provides the impedance measurement electrodes 130, and the top substrate 122 provides the test chemical 120. Thus, the bottom substrate 122 acts as an electrode substrate or electrode foil, whereas the top substrate or top substrates 122 may act as a cover foil and/or test chemical foil. Other embodiments are feasible. Thus, the test chemical 120 and the impedance measurement electrodes 130 may be provided on one and the same substrate and/or on different bottom substrates.

Figure 13:
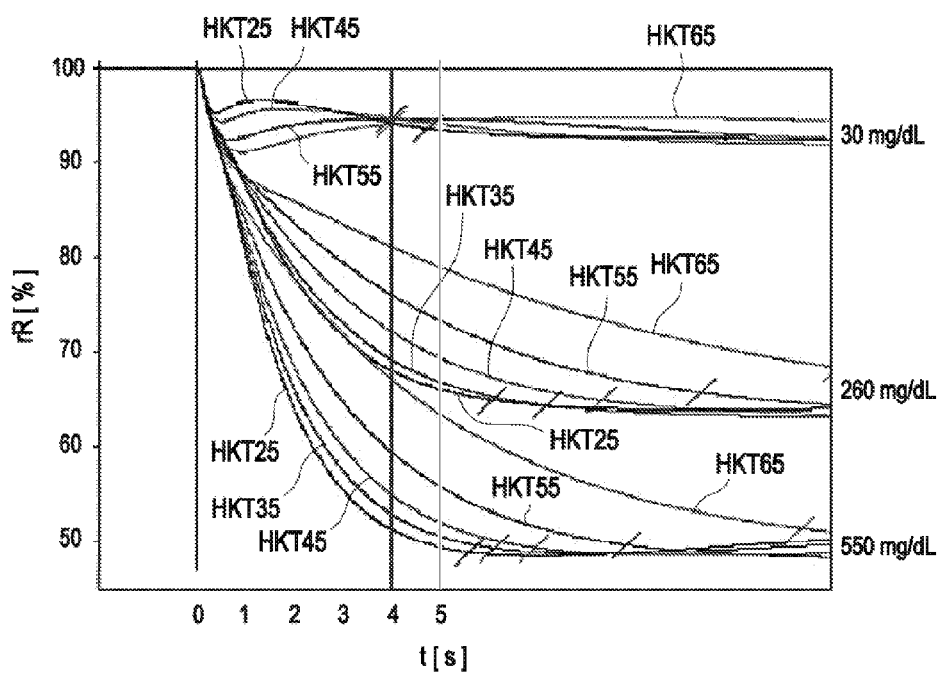
FIG. 13 shows an exemplary embodiment of determining a corrected value of a glucose concentration in whole blood, corrected for an actual hematocrit value.

In FIG. 13, an exemplary embodiment of providing a correction mechanism for determining a corrected value of a concentration of an analyte in a body fluid 112 is schematically depicted. In this exemplary embodiment, measurement curves of relative remission (rR), given in percent, are depicted, as a function of time t, given in seconds (s). The measurement curves are given for different hematocrit (HKT) values of 25%, 35%, 45%, 55% and 65% (denoted by HKT 25, HKT 35, HKT45, HKT55 and HKT 65, respectively), and for different glucose concentrations, in this case for 30 mg/dl, 260 mg/dl and 550 mg/dl.

As can be seen, the measurement curves are strongly dependent on the interferent concentration, in this case the HKT, and the concentration of the analyte, in this case glucose. As an example, optical measurement values may be derived from the measurement curves, which, as an example, are measurement values taken four seconds after initiation of the measurement (t=0 s). From these measurement curves, which may be provided as calibration curves, an estimated value of the glucose concentration may be derived. In a separate step, these estimated values may be corrected by an appropriate correction factor, in accordance with the hematocrit HKT. Thus, e.g. by using the method disclosed in conjunction with FIG. 3 and/or FIG. 7 above, the hematocrit HKT may be determined by performing an impedance measurement. By using the calibration curves in FIG. 13 and by using the estimated glucose concentration, an appropriate correction factor may be applied to the estimated glucose concentration, in order to derive a corrected value of the glucose concentration. This is depicted in Table 1:

TABLE 1

Examples of appropriate correction factors of estimated glucose concentrations for various hematocrit values. The correction is determined relatively to a "standard" hematocrit value of 45%. The correction factor is calculated as $(Remission_{HKT45} - Remission)/Remission_{HKT45}$.

| | 4 sec. reading time | | | | | |
|---|---|---|---|---|---|---|
| | 260 mg/dL Glucose | | | 550 mg/dL Glucose | | |
| Hematocrit | Remission | Diff Rem | Correction | Remission | Diff Rem | Correction |
| 25 | 68 | 4.2 | 6% | 51.3 | 3.7 | 7% |
| 35 | 69.5 | 2.7 | 4% | 53 | 2 | 4% |
| 45 | 72.2 | 0 | 0% | 55 | 0 | 0% |
| 55 | 76 | −3.8 | −5% | 59.5 | −4.5 | −8% |
| 65 | 81.2 | −9 | −12% | 67.3 | −12.3 | −22% |

Thus, in order to derive a corrected glucose concentration, the HKT may be derived by an appropriate impedance measurement. Further, an optical measurement value may be derived, such as by using a measurement value at a predetermined or determinable point in time after initiation of the measurement and/or an end point value.

The estimated glucose concentration derived by using this measurement value and/or the measurement value itself may be corrected by using an appropriate correction algorithm, such as by applying an appropriate correction factor, as outlined in Table 1. As an example, for a glucose concentration of 260 mg/dl and a hematocrit of 25%, a correction factor of +6% may be applied (compared to the glucose concentration measured for a sample with a "normal" HKT of 45%).

The above-mentioned exemplary embodiments widely relate to the use of aluminum as an electrode material for one or more of the impedance measurement electrodes 130. However, as outlined above, additionally or alternatively, one or more other materials may be used. Thus, preferably, at least one of the impedance measurement electrodes 130 comprises one or more metals selected from the group consisting of: aluminum, molybdenum, tungsten, tantalum, niobium, zirconium and titanium. Additionally or alternatively, even though less preferred, at least one metal selected from the group consisting of ruthenium, rhodium, iridium, palladium, platinum, silver and gold may be comprised.

Further, as outlined above, in case an alloy is used for one or more of the impedance measurement electrodes 130, one or more additives of metallic and/or nonmetallic nature may be present in the alloy. Potential additives which may be used are listed in the following overview: Lithium (Li), Sodium (Na), Potassium (K), Beryllium (Be), Magnesium (Mg), Calcium (Ca), Strontium (Sr), Scandium (Sc), Yttrium (Y), Titanium (Ti), Zirconium (Zr), Hafnium (Hf), Vanadium (V), Niobium (Nb), Tantalum (Ta), Chromium (Cr), Molybdenum (Mo), Tungsten (W), Manganese (Mn), Rhenium (Re), Iron (Fe), Ruthenium (Ru), Cobalt (Co), Rhodium (Rh), Iridium (Ir), Nickel (Ni), Palladium (Pd), Platinum (Pt), Copper (Cu), Silver (Ag), Gold (Au), Zinc (Zn), Boron (B), Indium (In), Silicium (Si), Germanium (Ge), Tin (Sn), Lead (Pb), Antimony (Sb), Bismuth (Bi), Selenium (Se), Tellurium (Te), Lanthanum (La), Cerium (Ce), Praseodymium (Pr), Neodymium (Nd), Samarium (Sm), Europium (Eu), Gadolinium (Gd), Terbium (Tb), Dysprosium (Dy), Holmium (Ho), Erbium (Er), Thulium (Tm), Ytterbium (Yb), Lutetium (Lu).

Figure 14:
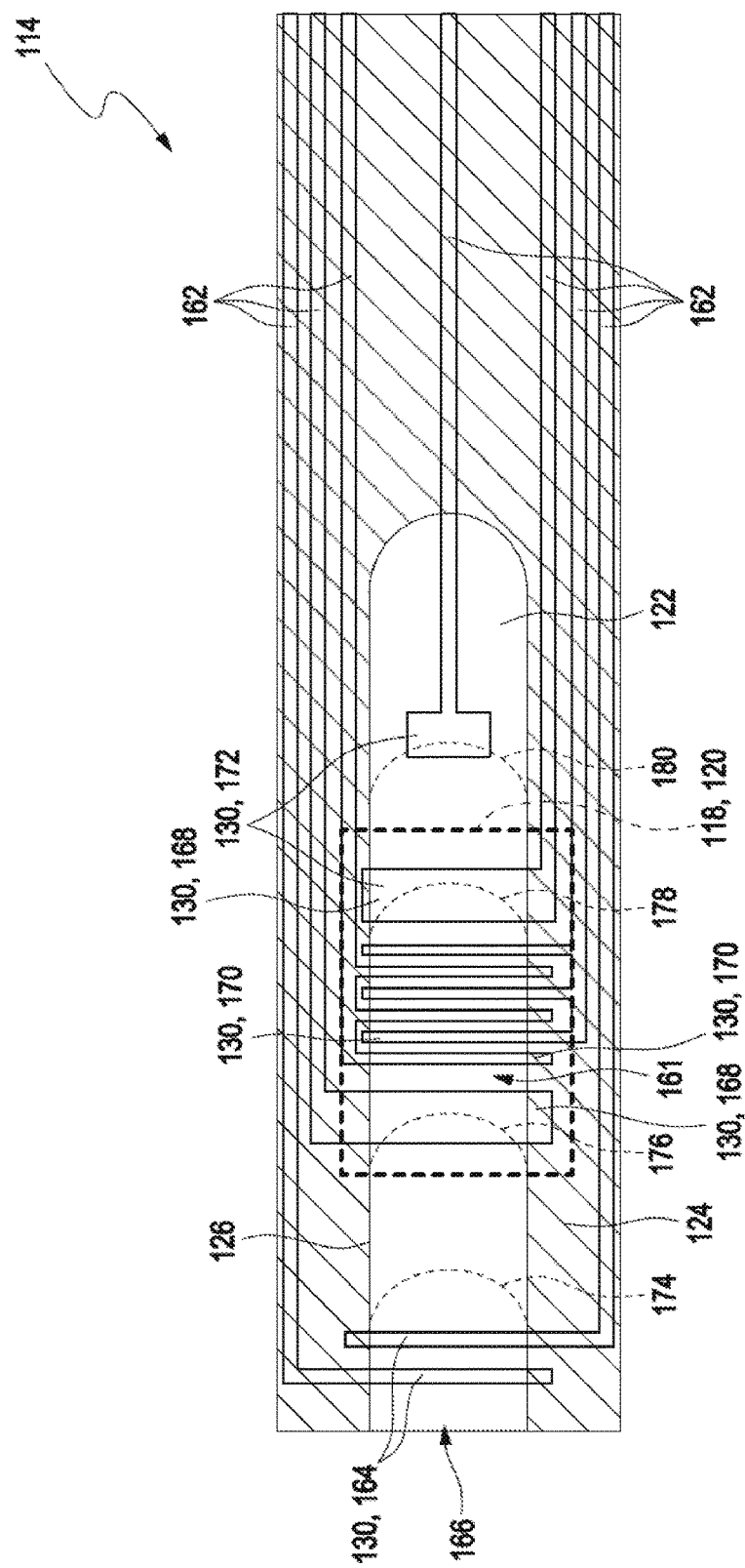
FIG. 14 shows an alternative setup of a test element.

In FIG. 14, a further embodiment of a test element 114 is shown in top view. Similar to the embodiment shown in FIGS. 11 and 12, the test element comprises a substrate 122 which partially is covered by a spacer 124 forming a capillary element 126. A cover foil, similar to the embodiment shown in FIG. 12, may further be present and is, however, not shown in FIG. 14.

The test element 114 further comprises a test field 118 having at least one test chemical 120. A region within the capillary element 126 covered by the test field 118 may be defined as a test zone 161. The test field 118, as an example, may be applied to one or both of the substrate 122 or the cover foil 160.

The test element 114 further comprises a plurality of impedance measurement electrodes 130 which may be contacted electrically via contact leads 162. Further, contact pads may be present, as in the setup shown in FIGS. 11 and 12, which, however, are not shown in the schematic drawing of FIG. 14.

The impedance measurement electrodes 130, in the setup of FIG. 14, may be adapted for various types of measurements, including measurements for performing one or more failsafe measurements such as in one or more failsafe steps.

Thus, in the exemplary embodiment shown in FIG. 14, a first pair 164 of measurement electrodes 130 may be present, close to an application opening 166 of the capillary element 126. This first pair 164 specifically may be adapted for dose detection. An increased conductivity between the electrodes of the first pair 164 may be measured when the first pair 164 is covered by a sample dose to the application opening 166. Thereby, a test sequence may be started, preferably automatically.

Further, the impedance measurement electrodes 130 may comprise a second pair 168 of measurement electrodes 130, specifically within the test field 118. The second pair 168 specifically may be a pair of macro bar electrodes. The second pair 168 specifically may be used for hematocrit detection. The electrodes of the second pair 168 may be spaced apart as far as possible within the test field 118. Due to this increased distance, the setup of the second pair 168 may specifically be sensitive to capillary height and hematocrit, since, due to the large distance between the electrodes of the second pair 168, a significant amount of blood cells may be accumulated between the electrodes.

Further, the impedance measurement electrodes 130 may comprise a third pair 170 of impedance measurement electrodes 130 located within the test field 118 which specifically may be sensitive to temperature and/or conductivity and less sensitive to other influences such as hematocrit. Thus, as an example, the third pair 170 may comprise interdigitating microelectrodes, such as two interdigitating comb-like electrode structures. Due to the frequent crossing of the capillary slide walls, these interdigitating microelectrodes may specifically be sensitive to the capillary width and, thus, may be sensitive to temperature and/or conductivity and less sensitive to hematocrit or other interferents. Those interdigitating microelectrodes can be used to assess the effect of temperature largely independent from the hematocrit effect on the impedance because the smaller gap between the comb-like electrode fingers reduces the impedance effect of the blood cell density.

Further, the impedance measurement electrodes 130 may comprise a fourth pair 172 of impedance measurement electrodes 130. As outlined above, two or more of the electrode pairs 164, 168, 170 or 172 may share one or more common electrodes. Thus, as shown in FIG. 14, the fourth pair 172 may share a downstream electrode of the second pair 168. The fourth pair 172 specifically may be adapted for wetting control or filling detection and may be adapted for detecting a complete filling of a test zone covering the test field 118. The fourth pair 172 specifically may work in combination with the first pair 164, for the purpose of wetting control and/or filling detection of the capillary element 126. Thus, in FIG. 14, four filling levels are symbolically depicted by dashed lines and denoted by reference numbers 174, 176, 178, 180. A first filling level 174 denotes a filling level at which dose detection by the first electrode pair 164 starts. The second filling level 176 denotes a filling level at which a test zone, defined by the test field 118, is reached. The third filling level 178 denotes a filling level at which an end of the test zone is reached. The fourth filling level 180 denotes a filling level at which a filling is complete or at least sufficient for measurements.

Thus, by using the electrode setup shown in FIG. 14, various failsafe mechanisms may be implemented, such as failsafe mechanisms relating to dosing and/or wetting and/or filling control and/or failsafe mechanisms relating to temperature and/or conductivity and/or hematocrit.

The measured impedance is sensitive to the geometry of the capillary (height, width), which can vary due to manufacturing tolerances. By usage of the differently structured electrode pairs, different interfering effects can be better separated and therefore compensated and/or measured.

The dose and fill electrode pairs 164, 172 specifically may be used to guarantee that the electrode pairs 168, 170, positioned in the test zone, are completely covered by the sample. The dose electrodes of the first pair 164 at the capillary entrance may be used to detect the first dosage and start the controlled test sequence. The geometrical factors of the respective cells, each cell comprising at least one electrode pair and a surrounding test chamber holding the liquid (surface, distance, arrangement, capillary width and height) contribute to the cell constant of the cell, as outlined above.

LIST OF REFERENCE NUMBERS

110 measurement system
112 body fluid
114 test element
116 measurement device
117 test element receptacle
118 test field
120 test chemical
122 substrate
124 spacer
126 capillary element
128 application location
130 impedance measurement electrodes
132 contact pads
134 detection window
136 optical detector
138 light source
140 light-sensitive element
142 impedance measurement device
144 contacting element
146 alternating electrical source
148 measurement device
150 evaluation unit
152 display
154 control element
156 electronic interface
158 casing
160 cover foil
161 test zone
162 contact leads
164 first pair of impedance measurement electrodes
166 application opening
168 second pair of impedance measurement electrodes
170 third pair of impedance measurement electrodes
172 fourth pair of impedance measurement electrodes
174 first filling level
176 second filling level
178 third filling level
180 fourth filling level

The invention claimed is:

1. A method for detecting at least one analyte in a body fluid, the method comprising the following steps:
   a) performing an optical measurement, wherein at least one test chemical is contacted with the body fluid, wherein the test chemical is an optical test chemical and is adapted to perform at least one detection reaction in the presence of the analyte, wherein at least one optically detectable property of at least one of the body fluid and the test chemical is changed due to the detection reaction, wherein at least, one optical measurement value is generated;
   b) performing at least one impedance measurement, wherein at least two impedance measurement electrodes are used, wherein at least one alternating electrical signal is applied to the body fluid via the impedance measurement electrodes land wherein at least one answer signal is recorded, wherein at least one impedance measurement value is generated;
   c) performing at least one evaluation step, wherein, in the evaluation step the optical measurement value and the impedance measurement value are used for detecting the analyte in the body fluid; and
   d) performing at least one failsafe step, wherein, in the failsafe step, only the impedance measurement value is used, the failsafe step comprising comparing one or both of a degree of filling of a capillary element and a degree of wetting of a test chemical with at least one threshold value.

2. The method according to claim 1 and further comprising performing a failsafe step comprising comparing at least one or both of an environmental parameter and a sample parameter to a threshold value.

3. The method according to claim 1, wherein in step c), detection of the analyte is performed as a detection of the concentration of the analyte in the body fluid and the concentration of the analyte in the body fluid is a corrected concentration which is corrected for at least one interferent concentration in the body fluid.

4. The method according to claim 1, wherein step c) comprises the following substeps:
   c.1) determining an estimated value of the concentration of the analyte in the body fluid by using the optical measurement value and
   c.2) determining a corrected value of the concentration of the analyte in the body fluid by using the estimated value and correcting the estimated value by using the impedance measurement value.

5. The method according to claim 4 wherein step c) comprises using a first evaluation algorithm, and further comprises using at least one correction algorithm using the impedance measurement.

6. The method according to claim 1, wherein a single test element is used for both method step a) and method step b).

7. The method according to claim 1, wherein at least one impedance measurement electrode of the at least two impedance measurement electrodes comprises a metal selected from the group consisting of: aluminum, molybdenum, tungsten, tantalum, niobium, zirconium, titanium, ruthenium, rhodium, iridium, palladium, platinum, silver, and gold.

8. The method according to claim 1, wherein at least one impedance measurement electrode of the at least two impedance measurement electrodes comprises aluminum.

9. The method according to claim 1, wherein step d) comprises using the impedance measurement value to determine the wetting of at least, one of the impedance measurement electrodes, the test chemical and a capillary element.

10. The method according to claim 1 and further comprising performing a failsafe step comprising comparing the temperature of a surrounding environment to a threshold value.

11. The method according, to claim 1 and further comprising performing a failsafe step comprising, comparing a sample temperature to a threshold value.

12. The method of claim 1, wherein the at least two impedance measurement electrodes provide the at least one impedance measurement value used for determining the concentration of the analyte in the body fluid and the at least two impedance measurement electrodes further are used for providing at least one wetting information, wherein the wetting information comprises at least one item of information regarding a wetting of at least one of the test element, a capillary element of the test element, the test chemical and the impedance measurement electrodes with the body fluid.

13. A method for, detecting the concentration of at least one, analyte in a body fluid, the method comprising:
   a) performing an optical measurement, wherein at least one test chemical is contacted with the body fluid, wherein the test chemical is an optical test chemical and is adapted to, perform at least one detection reaction in the presence of the analyte, wherein at least one optically detectable property of at least one of the body fluid and the test chemical is changed due to the detection reaction, wherein at least one optical measurement value is generated;
   b) performing at least one impedance measurement, wherein at least two impedance measurement electrodes are used, wherein at least one alternating electrical signal is applied to the body fluid via the impedance measurement electrodes and wherein at least one answer signal is recorded, wherein at least one impedance measurement value is generated;
   c) performing at least one evaluation step, wherein, in the evaluation step the optical measurement value and the impedance measurement value are used for determining a concentration of the analyte in the body fluid; and
   d) performing at least one failsafe step, wherein, in the failsafe step, only the impedance measurement value is used, the failsafe step comprising comparing one or both of a degree of filling of a capillary element and a degree of wetting of a test chemical with at least one threshold value.

14. The method according to claim 13 wherein step c) comprises using the optical measurement value to determine an estimated concentration and correcting the estimated concentration from the optical measurement value to optical for at least one interferent concentration.

15. The method according to claim 14 which comprises correcting the estimated concentration for hematocrit concentration.

* * * * *